United States Patent
Fuerstner et al.

(10) Patent No.: US 8,993,470 B2
(45) Date of Patent: Mar. 31, 2015

(54) CATALYSTS FOR THE ALKYNE METATHESIS

(75) Inventors: Alois Fuerstner, Muelheim an der Ruhr (DE); Johannes Heppekausen, Muelheim an der Ruhr (DE); Volker Hickmann, Dannstadt (DE); Robert Stade, Muelheim an der Ruhr (DE)

(73) Assignee: Studiengesellschaft Kohle mbH (DE)

( * ) Notice: Subject to any disclaimer, the term of this patent is extended or adjusted under 35 U.S.C. 154(b) by 414 days.

(21) Appl. No.: 13/639,067

(22) PCT Filed: Mar. 31, 2011

(86) PCT No.: PCT/DE2011/000348
§ 371 (c)(1),
(2), (4) Date: Nov. 26, 2012

(87) PCT Pub. No.: WO2011/120508
PCT Pub. Date: Oct. 6, 2011

(65) Prior Publication Data
US 2013/0144102 A1 Jun. 6, 2013

(30) Foreign Application Priority Data

Apr. 3, 2010 (DE) .......................... 10 2010 013 813
Jun. 10, 2010 (DE) .......................... 10 2010 023 326

(51) Int. Cl.
| | | |
|---|---|---|
| C07C 6/04 | (2006.01) | |
| B01J 31/22 | (2006.01) | |
| B01J 31/18 | (2006.01) | |
| C07F 11/00 | (2006.01) | |
| C08F 4/72 | (2006.01) | |
| C07C 6/02 | (2006.01) | |

(52) U.S. Cl.
CPC ............ *B01J 31/2295* (2013.01); *C07F 11/00* (2013.01); *C07F 11/005* (2013.01); *C08F 4/72* (2013.01); *B01J 31/2286* (2013.01); *C07C 6/02* (2013.01)
USPC ........... 502/158; 502/151; 502/152; 502/155; 585/646; 585/645

(58) Field of Classification Search
USPC ........... 502/151, 152, 155, 158; 585/646, 645
See application file for complete search history.

(56) References Cited

U.S. PATENT DOCUMENTS

| | | |
|---|---|---|
| 6,121,473 A | 9/2000 | Schrock et al. |
| 2008/0119678 A1 | 5/2008 | Hock et al. |
| 2011/0015430 A1 | 1/2011 | Schrock et al. |
| 2011/0077421 A1 | 3/2011 | Schrock et al. |

FOREIGN PATENT DOCUMENTS

WO WO2011/007742 8/2011

OTHER PUBLICATIONS

Tsai et al., 'Facile Synthesis of Trialkoxymolybdenum (VI) Alkylidyne Complexes for Alkyne Metathesis', Organmetallics 2000, vol. 19, No. 25, 5260-5262.
Heppekausen et al. 'Practical New Sulyloxy-Based Alkyne Metathesis Catalysts with Optimized Activity and Selectivity Profiles', J Am Chem Soc, 2010, vol. 132, No. 32, 11045-11057.
Extended European Search Report dated Nov. 6, 2013 for 13001297.4.
Schrock, 'Recent Advances in High Oxidation State Mo and W Imido Alkylidene Chemistry', Chemical Reviews, vol. 109 No. 8, Mar. 13, 2009.
'Marinescu et al., 'Ethenolysis Reactions Catalyzed by Imido alkylinene Monoaryloxide Monopyrrolide (MAP) Complexes of Molybdenum', Journal of the American Chemical Society, ACS Publications, US, vol. 131, No. 31, Aug. 12, 2009, pp. 10840-10841.
Yu et al., 'Enol Ethers as Substrates for Efficient Z—and Enantioselective Ring-Opening/Cross-Metathesis Reactions Promoted by Steriogenic-at-Mo Complexes: Utility in Chemical Synthesis and Mechanistic Attributes', Journal of the American Chemical Society, vol. 134, No. 5, Jan. 24, 2012, pp. 2788-2799.
Bailey et al., 'Evaluation of Molybdenum and Tungsten Metathesis Catalysts for Homogeneous Tandem Alkane Metathesis', Organometallics, vol. 28, No. 1, Dec. 12, 2008, pp. 355-360.
Marinescu et al., 'Simple Molybdenum (IV) Olefin Complexes of the Type Mo (NR) (X) (Y) (olefin)', Organometiallics, vol. 29, No. 24, Dec. 2, 2010, pp. 6816-6828.
Yu et al., 'Synthesis of Macrocyclic Natural Products by Catalyst-Controlled Stereoselective Ring-Closing Metathesis', Nature, vol. 479, No. 7371, Nov. 2, 2011, pp. 89-93.
Jiang et al., 'Highly Z-Selective Metathesis Homocoupling of Terminal Olefins', Journal of the American Chemical Society ACS Publications, US, vol. 131, No. 46, Nov. 25, 2009, pp. 16630-16631.
Lee et al., 'Endo-Selective Enyne Ring-Closing Metathesis Promoted by Steriogenic-at-Mo Monoalkoxide and Monoaryloxide Complexes. Efficient Synthesis of Cyclic Dienes Not Accessible Through Reactions with Ru Carbenes', Journal of the American Chemical Society, vol. 131, No. 30, Jul. 6, 2009, pp. 10652-10661.
U.S. Appl. No. 14/001,811, filed Jun. 6, 2013, Fuerstner et al.
U.S. Appl. No. 14/209,313, filed Mar. 13, 2014, Ondi et al.

*Primary Examiner* — Thuan D Dang
(74) *Attorney, Agent, or Firm* — Stoel Rives LLP

(57) ABSTRACT

Organometallic compounds of the general formula (I), in which M=Mo, W, are claimed.

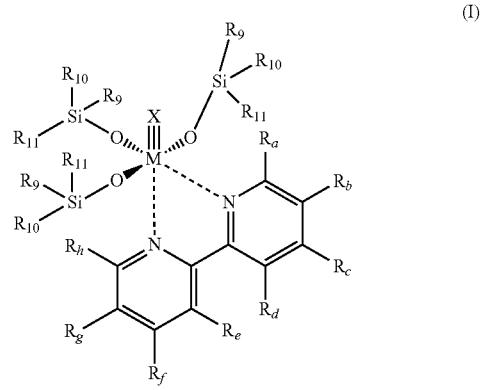

(I)

25 Claims, 7 Drawing Sheets

Structure of Mo(≡N)(OSiPh$_3$)$_3$(phen) in solids

Structure of Mo(≡CtBu)(OSiPh$_3$)$_3$(MeCN) in solids

Structure of Mo(≡CPh)(OSiPh₃)₃(phen) in solids

Structure of [W(≡CAr)(OSiPh₃)₃(phen)] in solids

Figure 1:
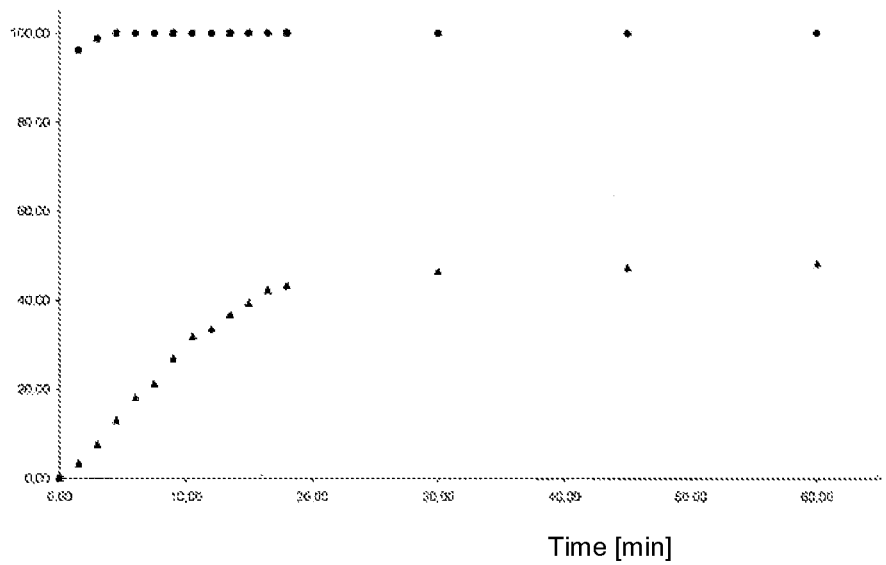

Structure of Mo(≡CAr)(OSiPh₃)₃ in solids, wherein Ar = 2,6-dimethylphenyl

Structure of [Mo(≡CAr)(OSiPh₃)₃·(phen) in solids, wherein Ar = 2,6-dimethylphenyl.
The crystal contains co-crystallized CH₂Cl₂.

Structure of [Mo(≡N)(OSiPh$_3$)$_3$(bipy)] in solids

Structure of [Mo(≡N)(OSiPh$_3$)$_3$(4,4'-di-tert-butyl-2,2'-dipyridyl)] (24) in solids Structure of [Mo(≡CPh)(OSiPh$_3$)$_3$(bipy)] in solids Structure of [Mo(≡CPh)(OSiPh$_3$)$_3$(4,4'-dimethoxy-2,2'-dipyridyl)] in solids Structure of [Mo(≡CPh)(OSiAr$_3$)$_3$·(bipy)] in solids, wherein Ar = 4-methoxyphenyl

CATALYSTS FOR THE ALKYNE METATHESIS

CROSS-REFERENCE TO RELATED APPLICATIONS

This application is a national stage application under 35 U.S.C. §371 of International Application No. PCT/DE2011/000348, titled CATALYSTS FOR THE ALKYNE METATHESIS, filed Mar. 31, 2011, which claims priority to German Application No. 102010013813.4, filed Apr. 3, 2010, and from German Application No. 102010023326.9, filed Jun. 10, 2010, all of which are hereby incorporated by reference in their entireties.

The present invention relates to metal-organic W- and Mo-complexes, a method for the preparation thereof and the use as pre-catalysts and catalysts for the alkyne metathesis.

By alkyne metathesis there is understood the mutual transalkylidynation of alkynes according to Scheme 1. Alkyne metathesis can be performed intermolecularly as well as intramolecularly (Fürstner, A.; Davies, P. W. *Chem. Commun.* 2005, 2307; Zhang, W.; Moore, J. S. *Adv. Synth. Catal.* 2007, 349, 93; Schrock, R. R.; Czekelius, C. *Adv. Synth. Catal.* 2007, 349, 55).

Scheme 1. Principle of alkyne methathesis.

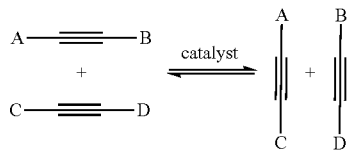

Alkyne metathesis reactions are catalyzed by metal compounds, which may be present in the reaction mixture in homogeneous or in heterogeneous form. According to the literature, the most frequently used compounds are metal compounds of tungsten, molybdenum and rhenium. The really catalytically active species are the so-called Schrock-Alkylidyne complexes (Schrock, R. R. *Chem. Ref.* 2002, 102, 145; Schrock, R. R. *Angew. Chem., Ind. Ed.* 2006, 45, 3748) which may be prepared in situ or ex situ. The until now used Schrock-Alkylidyne complexes, however, as a rule, react both as solids and in solution rapidly with oxygen and/or moisture while forming catalytically inactive species, and thus must be handled by rigorously excluding air and moisture. Representative examples are listed in Scheme 2.

Contrary to this, alkylidyne complexes ("Fischer-Carbynes", see: Fischer, E. O., *Adv. Organomet. Chem.* 1976, 14, 1), which have at the metal center one or more carbon monoxide ligands (CO), may be stabilized by oxygen-, nitrogen-, or phosphor-containing ligands. The such obtained Fischer-Carbynes are even partially stable when exposed to air (Mayr, A. et al. *Organometallics* 1985, 4, 608; Hazra, D. et al., *J. Organomet. Chem.* 2003, 671, 52), however, do not show catalytic activity in the alkyne metathesis.

Scheme 2. Representative examples for pre-catalysts and Schrock-Alkylidyne complexes for the alkyne metathesis.

1

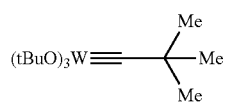

2

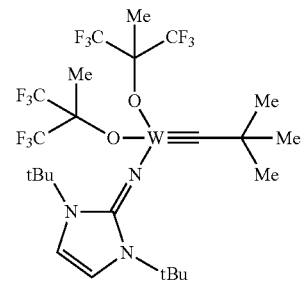

3

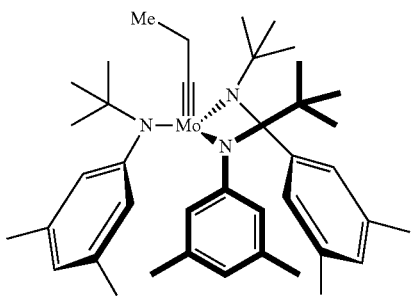

4

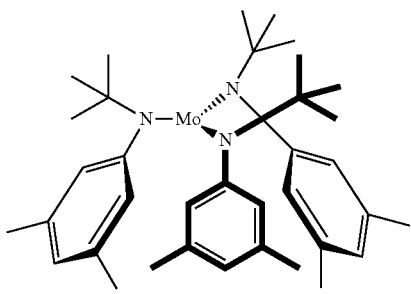

Although catalytically active Schrock-Alkylidyne complexes may be produced in the reaction mixture in situ from suitable pre-catalysts, also for these indirect methods mostly likewise rigorous conditions have to be applied with regard to the exclusion of air and moisture. This applies e.g. for the use of molybdenum trisamido complexes of type 4, from which by means of reaction with halogen compounds in situ catalytically active molybdenum alkylidynes are formed (Fürstner, A. et al. *J. Am. Chem. Soc.* 1999, 121, 9453; Zhang, W. et al. *J. Am. Chem. Soc.* 2004, 126, 329). Pre-catalyst 4 does not only react with air and water, however, amongst others, activates also molecular nitrogen ($N_2$) such that even the usual working techniques using nitrogen as inert gas may not be applied, but argon has to be applied as inert gas. The use of 4 as pre-catalyst, however, has made possible numerous applications of the alkyne metathesis to highly functionalized substrates and natural materials for which other alkyne metathesis catalysts were not suitable (Fürstner, A. et al. *Chem. Eur. J.* 2001, 7, 5299; Fürstner, A. et al. *W. Chem. Commun.* 2005, 2307).

User-friendly recipes for the preparation of catalysts for the alkyne metathesis in situ use mixtures of molybdenum or tungsten compounds in combination with diverse additives. Typical methods use, amongst others, combinations of $Mo(CO)_6$/phenol or substituted phenols and $MoO_2(acac)_2$/$Et_3Al$, $MoO_3/SiO_2$, $WO_3/SiO_2$ (review: Mortreux, A. et al. *J. Mol. Catal.* 2006, 254, 96). However, these methods mostly tolerate only few functional groups. Also, as a rule, the alkyne metathesis reactions must be performed at high temperatures, which exclude applications to highly functionalized and thermally unstable substrates.

Scheme 3. Preparation of metal alkylidyne complexes from metal nitrido complexes; R = alkyl, aryl.

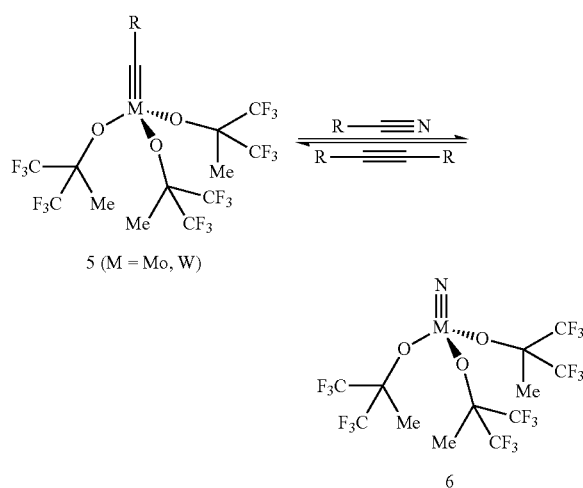

Alternatively, catalytically active Schrock-Alkylidyne complexes may be prepared in situ by reaction of metal nitrido complexes as pre-catalysts with alkynes (Scheme 3). However, this requires specific alkoxyde ligands in the coordination sphere of the pre-catalyst, wherein highly fluorinated or per-fluorinated, mostly branched alkoxides (e.g. per-fluoro-tert-butanolate, hexafluoro-tert-butanolate) have proved to be particularly suitable (Geyer A. M. et al., *J. Am. Chem. Soc.* 2008, 130, 8984; Gdula, R. L. et al. *J. Am. Chem. Soc.* 2006, 128, 9614).

Scheme 4. Use of metal nitrido complexes with silanolate ligands as pre-catalysts; R = alkyl, aryl.

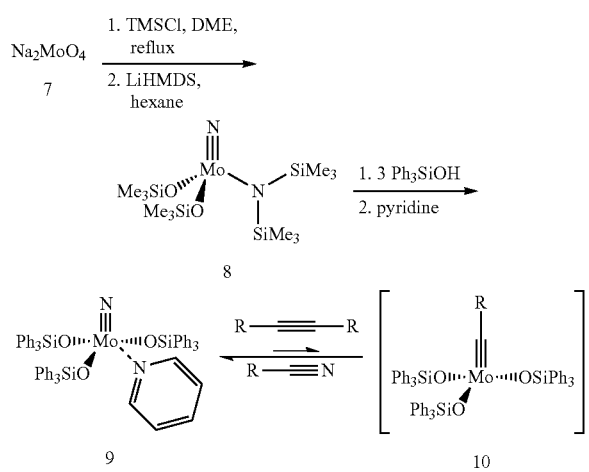

It is further known that also metal nitrido complexes of tungsten or molybdenum with silanolate ligands are useful for preparing active catalysts for the alkyne metathesis; in doing so, the in situ formation of alkylidyne complexes of type 10 is postulated, without that this aspect could be unambiguously clarified by means of isolation or characterization of the active species (Fürstner, A. et al, *J. Am. Chem. Soc.* 2009, 131, 9468; Heilmann, E., Dissertation, Technische Universität Dortmund, 2008; Bindl, M., Technische Universität Dortmund, 2009). If such a pre-catalyst is stabilized with an additional pyridine ligand as is shown at the example of compound 9 (Scheme 4), then, this may be handled at air for a short time. However, a storage under air leads in less than 30 minutes to the decomposition and to a complete loss of the catalytic activity.

Surprisingly, it turned out that the nitrido complexes of molybdenum and tungsten, which bear in place of a simple pyridine ligand a bridged ligand such as 2,2'-bipyridine, 1,10-phenanthroline or derivatives thereof, contrary to compound 9, may be stored at air over months without decomposition without that measures for the exclusion of moisture have to be taken. Although said complexes as such have no or only low catalytic activity in the alkyne metathesis of 1-phenyl-1-propine under conditions at which, for example, the pyridine complex 9 results in tolane in high yields (toluene, 80° C.), however, we discovered that from nitrido complexes of molybdenum and tungsten with stabilizing 2,2'-bipyridine or 1,10-phenanthroline ligands by addition of suitable metal salts as additives active catalysts for the alkyne metathesis may be generated. Likewise, also by means of 2,2'-bipyridine or 1,10-phenanthroline ligands also Schrock-Alkylidyne complexes can be stabilized. However, these educts also have no or only low activity as catalysts for the alkyne metathesis. However, it could be shown that also from these adducts by addition of suitable metal salts as additives active catalysts may be released for the alkyne metathesis.

Accordingly, an object of the present invention are metal-organic compounds of the general Formula I, (1)

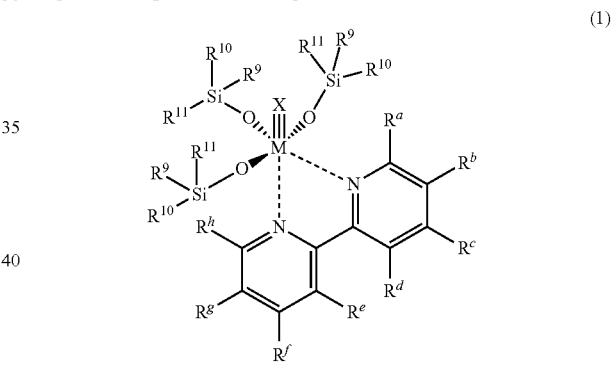

wherein
M=Mo, W,
the substituents $R^a$, $R^b$, $R^c$, $R^d$, $R^e$, $R^f$, $R^g$, $R^h$ may be equal or may be different from one another and may be independently selected from one another from: H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, nitro, cyano, trifluoromethyl, —COOR$^{12}$, wherein $R^{12}$=$C_1$-$C_{12}$ alkyl, $C_3$-$C_{12}$ cycloalkyl, 6-18 membered aryl, 5-10 membered heteroaryl, and the substituents $R^a$ and $R^b$ or $R^b$ and $R^c$ or $R^c$ and $R^d$ as well as $R^h$ and $R^g$ or $R^g$ and $R^f$ or $R^f$ and $R^e$ also may be linked to one another while forming a saturated, unsaturated or aromatic ring, and/or the residues $R^d$ and $R^e$ may be linked to one another by forming a 5-8 membered saturated, unsaturated, or aromatic ring, the substituents $R^9$, $R^{10}$, $R^{11}$ may be equal or may be different from one another and may be independently selected from one another from the following groups: $C_1$-$C_{12}$-alkyl, $C_3$-$C_{12}$-cycloalkyl, 6-18 membered aryl, 5-10 membered heteroaryl, $C_3$-$C_{12}$-cycloalkyl, 6-18 membered aryl, 5-10 membered heteroaryl, with the proviso that at least one of said substituents is a 6-18 membered aryl or 5-10 membered heteroaryl residue, wherein said aryl or heteroaryl residue may in turn have at the silicon up to five identical or different substituents, from the list: H, $C_1$-$C_{12}$-alkyl, $C_1$-$C_{12}$-alkoxy, di-$C_1$-$C_4$-alkylamino, $C_3$-$C_{12}$-cycloalkyl, $C_3$-$C_{12}$-cycloalkyloxy, 6-8 membered aryl, 5-10 membered heteroaryl, halogen, and X=N, $CR^{13}$, wherein $R^{13}$=$C_1$-$C_{12}$-alkyl, $C_3$-$C_{12}$-cycloalkyl, 6-18 membered aryl, 5-10 membered heteroaryl.

The residues $R^d$ and $R^e$ may also be linked to one another such that they form a 5-8 membered saturated, unsaturated or aromatic ring and thus form a bridge, which may be $CR^{41}R^{42}$, $CR^{43}$=$CR^{44}$, $CR^{45}R^{46}$—$CR^{47}R^{48}$, $CR^{49}R^{50}$—$R^{51}R^{52}$—$CR^{53}R^{54}$, $CR^{55}R^{56}$=$C^{57}R^{58}$—$CR^{59}R^{60}$, $CR^{61}R^{62}$—$CR^{63}R^{65}$—$CR^{65}R^{66}$—$CR^{67}CR^{68}$, $CR^{69}$=$CR^{70}$—$CR^{71}R^{72}$—$CR^{73}CR^{74}$ or $CR^{75}R^{76}$—$CR^{77}$=$CR^{78}$—$CR^{79}CR^{80}$, in which $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$ and $R^{80}$ may be independently selected from one another and may have the same meaning as $R^a$.

If the residues $R^d$ and $R^e$ stand for a non-bridged group, then the ligand is a 2,2'-bipyridine derivative (2,2'-dipyridyl derivative).

Preferred compounds of Formula I are represented by the general Formula 11

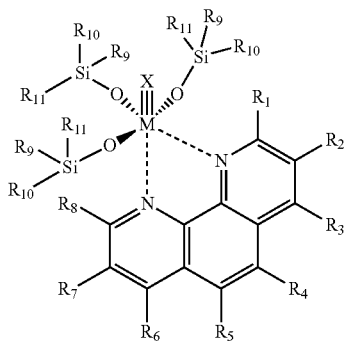

11 wherein
the substituents $R^1$, $R^2$, $R^3$, $R^4$, $R^5$, $R^6$, $R^7$, $R^8$ may be equal or may be different from one another and may be independently selected from one another from: H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, nitro,
M, X, $R^9$, $R^{10}$ and $R^{11}$ are defined as defined above.
Further preferred compounds are such compounds, which are represented by the general Formula 11a

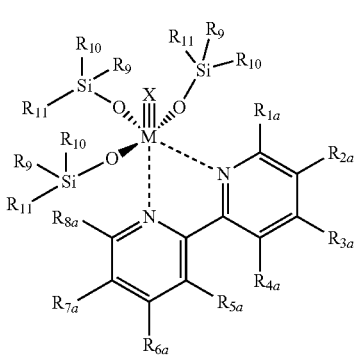

11a wherein
$R^{1a}$, $R^{2a}$, $R^{3a}$, $R^{4a}$, $R^{5a}$, $R^{6a}$, $R^{7a}$, $R^{8a}$ have the same meaning as is defined for $R^1$, $R^2$, $R^3$, $R^4$, $R^5$, $R^6$, $R^7$, $R^8$ in Formula 11, and
M, X, $R^9$, $R^{10}$ and $R^{11}$ are defined as defined above.
In the context of the present invention, the following terms mean:

$C_1$-$C_{12}$-alkyl, a linear or branched alkyl residue having 1 to 12 carbon atoms;

$C_1$-$C_{12}$-alkoxy, a linear or branched alkoxy residue having 1 to 12 carbon atoms;

Di-$C_1$-$C_4$-alkylamino, an amino group having two identical or different linear or branched alkyl substituents, which have from 1 to 4 carbon atoms, respectively;

$C_3$-$C_{12}$-cycloalkyl, a monocyclic, saturated cycloalkyl group having 3 to 12 carbon atoms;

$C_3$-$C_{12}$-cycloalkyloxy, a monocyclic, saturated cycloalkyloxy group having 3 to 12 carbon atoms;

6-18 membered aryl, a mono-, bi- or tricyclic carbocyclic aromatic compound, which in turn may bear from 0 to 5 substituents from the list: $C_1$-$C_{12}$-alkyl, $C_1$-$C_{12}$-alkoxy, di-$C_1$-$C_4$-alkylamino, $C_3$-$C_{12}$-cycloalklyl, $C_3$-$C_{12}$-cycloalkyloxy, 6-18 membered aryl, 5-10 membered heteroaryl, halogen, cyano, nitro;

5-10 membered heteroaryl, a mono- or, as the case may be, bicyclic aromatic heterocycle (heteroaromatic compound) with all in all from 5 to 10 ring atoms, which contains up to three ring heteroatoms from the row N, O and/or S, and is linked via a ring carbon atom or, as the case may be, via a ring nitrogen atom. Exemplarily mentioned are: Furyl, pyrrolyl, thienyl, pyrazolyl, imidadozly, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzoimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl.

Halogen means in the context of the invention fluorine, chlorine, bromine and iodine.

Preferred alkyl residues in the context of this invention are linear or branched alkyl residues having 1 to 6 carbon atoms. Exemplarily and preferably mentioned are: Methyl, ethyl, n-propyl, isopropyl, n-butyl, iso-butyl, sec.-butyl, tert.-butyl, 1-ethylpropyl, n-pentyl and n-hexyl.

Preferred alkoxy residues in the context of this invention are linear or branched alkoxy residues having 1 to 6 carbon atoms. Exemplarily and preferably mentioned are: Methoxy, ethoxy, n-propoxy, isopropoxy, n-butoxy, tert.-butoxy, n-pentoxy and n-hexoxy.

Preferred cycloalkyl residues in the context of this invention are the cycloalkyl residues having 3 to 7 carbon atoms. Exemplarily and preferably mentioned are: Cyclopropyl, cyclobutyl, cyclopentyl, cyclohexyl and cycloheptyl.

Preferred cycloalkyloxy residues in the context of this invention are cycloalkyloxy residues having 3 to 7 carbon atoms. Exemplarily and preferably mentioned are: cyclopropyloxy, cyclobutyloxy, cyclopentyloxy, cyclohexyloxy and cycloheptyloxy.

Preferred di-$C_1$-$C_4$-alkylamino residues in the context of this invention are the following di-$C_1$-$C_4$-alkylamino residues: N,N-dimethylamino, N,N-diethylamino, N-ethly-N-methylamino, N-methyl-N-n-propylamino, N-isopropyl-N-methylamino, N-isopropyl-N-ethylamino, N-isopropyl-N-n-propylamino, N,N-diisopropylamino, N-n-butly-N-methylamino and N-tert.-butyl-N-methylamino.

Preferred aryl residues in the context of this invention are: Phenyl, naphthyl, anthryl, methylphenyl, dimethylphenyl, trimethylphenyl, methoxyphenyl, dimethoxyphenyl, trimethoxyphenyl, fluorophenyl, chlorophenyl, bromophenyl, iodophenyl, pentafluorophenyl, trifluoromethylphenyl, dimethylaminophenyl, $C_1$-$C_{12}$-alkoxycarbonylphenyl.

Preferred heteroaromatic residues in the context of this invention are mono- or, as the case may be, bicylcic 5-10 membered heteroaryl residues having up to two heteroatoms from the row N, O and/or S. Particularly preferred are monocyclic 5- or 6-membered heteroaryl residues having up to two heteroatoms from the row N, O and/or S such as furyl, thienyl, thiazolyl, oxazolyl, isothiazolyl, isoxazolyl, pyrazolyl, imidazolyl, pyridyl, pyrimidinyl, pyridazinyl, pyrazinyl.

Examples for preferred silanolate ligands of the general type $R^9R^{10}R^{11}SiO$— are in the context of this invention: Triphenyl silanolate, phenyldimethyl silanolate, phenyldi(tert.-butyl)silanolate, diphenylmethyl silanolate, diphenyl(tert.-butyl)silanolate, tris(methoxypenyl)silanolate, tris(dimethoxyphenly) silanolate, tris(dimethylphenyl) silanolate, tris(trimethylphenyl)silanolate, tris(dimethylaminophenyl)silanolate, tris(fluorophenyl)silanolate, tris(difluorophenyl)silanolate, tris(pentafluorophenyl)silanolate, tris(3,5-di-tert.-butyl-6-methoxyphenyl)silanolate, tris(1-naphthyl)silanolate, tris(2-furyl)silanolate, tris(2-thienyl)silanolate.

Preferred compounds in the context of the present invention are complexes of the general Formula 12:

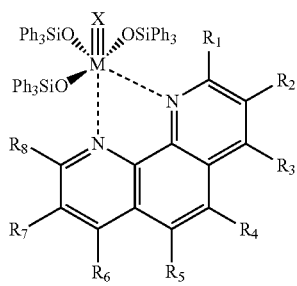

12 wherein

M=Mo, W

X=N, $CR^{13}$, wherein $R^{13}$ is methyl, ethyl, propyl, butyl, isopropyl, tert-butyl, trimethylsilylmethyl, benzyl, furyl, phenyl, wherein in turn phenyl may bear up to five identical or different residues from the list: H, methyl, ethyl, propyl, butyl, tert.-butyl, iso-propyl, phenyl, fluorine, chlorine, trifluoromethyl, methoxy, ethoxy, dimethylamino, diethylamino, trimethylsilyl, $R^1$, $R^2$, $R^3$, $R^4$, $R^5$, $R^6$, $R^7$, $R^8$ may be freely and independently selected from one another from: H, $C_1$-$C_4$ alkyl, $C_3$-$C_6$ cycloalkyl, phenyl, naphthyl, methylphenyl, dimethylphenyl, trimethylphenyl, methoxyphenyl, dimethoxyphenyl, fluorophenyl, pentafluorophenyl, trifluoromethylphenyl, dimethylaminophenyl, furyl, halogen, nitro, cyano, trifluoromethyl, —$COOR^{12}$, wherein $R^{12}$=$C_1$-$C_{12}$ alkyl, $C_3$-$C_{12}$ cycloalkyl, 6-18 membered aryl, 5-10 membered heteroaryl; preferred are methyl, ethyl, propyl, isopropyl, butyl, tert.-butyl, pentyl, hexyl, heptyl, octyl, benzyl, phenyl.

Examples for preferred 1,10-phenanthrolines are: The unsubstituted 1,10-phenanthroline, 4-methyl-1,10-phenanthroline, 5-methyl-1,10-phenanthroline, 2,9-dimethyl[1,10]phenanthroline, 5,6-dimethyl-1,10-phenanthroline, 5-chloro[1,10]phenanthroline, 4,7-dichloro-1,10-phenanthroline, 4,7-dichloro-1,10-phenanthroline, 3,4,7,8-tetramethyl-1,10-phenanthroline, 4,7-diphenyl[1,10]phenanthroline, 2,9-dimethyl-4,7-diphenyl[1,10]phenanthroline, 5-nitro-1,10-phenantroline, 4,7-dimethoxy-1,10-phenanthroline.

Likewise preferred compounds in the context of the present invention are complexes of the general Formula 12a:

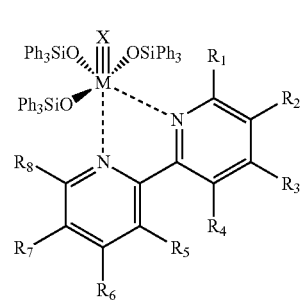

12a wherein

M=Mo, W

X=N, $CR^{13}$, wherein $R^{13}$ may be methyl, ethyl, propyl, butyl, isopropyl, tert-butyl, trimethylsilylmethyl, benzyl, furyl, phenyl, wherein phenyl in turn may bear up to five identical or different residues from the list: H, methyl, ethyl, propyl, butyl, tert.-butyl, isopropyl, phenyl, fluorine, chlorine, trifluoromethyl, methoxy, ethoxy, dimethylamino, diethylamino, trimethylsilyl, $R_1$, $R_2$, $R_3$, $R_4$, $R_5$, $R_6$, $R_7$, $R_8$ may be freely and independently selected from one another from: H, $C_1$-$C_4$ alkyl, $C_3$-$C_6$ cycloalkyl, phenyl, naphthyl, methylphenyl, dimethylphenyl, trimethylphenyl, methoxyphenyl, dimethoxyphenyl, fluorophenyl, pentafluorophenyl, trifluoromethylphenyl, dimethylaminophenyl, furyl, halogen, nitro, —$COOR^{12}$, wherein $R^{12}$=$C_1$-$C_{12}$ alkyl, $C_3$-$C_{12}$ cycloalkyl, 6-18 membered aryl, 5-10 membered heteroaryl; preferred are methyl, ethyl, propyl, isopropyl, butyl, tert.-butyl, pentyl, hexyl, heptyl, octyl, benzyl, phenyl.

Examples for preferred 2,2'-bipyridines (2,2'-dipyridyls) are: 2,2'-bipyridine, 5,5'-dimethyl-2,2'-dipyridyl, 4,4'-dimethyl-2,2'-dipyridyl, 6,6'-dimethyl-2,2'-dipyridyl, 4,4'-dimethoxy-2,2'-bipyridine, 2,2'-biquinoline, 4,4'-di-tert.-butyl-2,2'-dipyridyl, 2,2'-bipyridinyl-4,4'-dicarboxylic acid dimethyl ester, 4,4'-diphenyl-2,2'-dipyridyl, 6,6'-dibromo-2,2'-dipyridyl, 4,4'-dinonyl-2,2'-dipyridyl, 2,2'-biquinolinyl-4,4'-dicarboxylic acid dibutyl ester, 2,2'-biquinolinyl-4,4'-dicarboxylic acid diheptyl ester, 6-methyl-2,2'-dipyridyl, 2-(2-pyridinyl)quinoline, 2-pyridin-2-yl-4-pyrrolidin-1-yl-quinoline, 4-piperidin-1-yl-2-pyridin-2-yl-quinoline, 4-morpholin-4-yl-2-pyridin-2-yl-quinoline.

Particularly preferred compounds in the context of the present invention are complexes of Formulas 13a, 13b, 14a, 14b, 15a, 15b, 16a, 16b, 13e:

13a
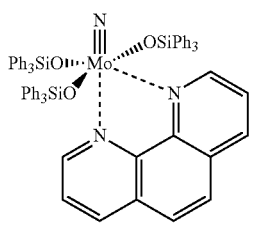
14a
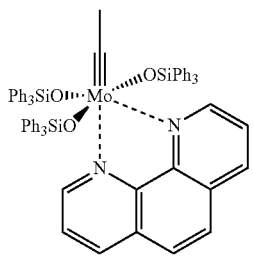
15a
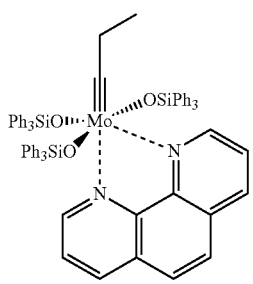
16a
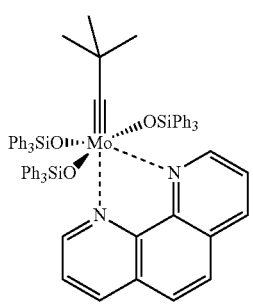
13b
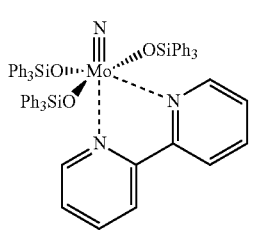
14b
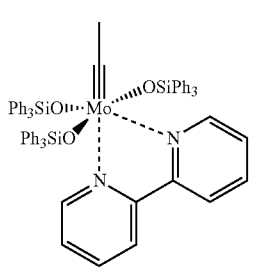
15b
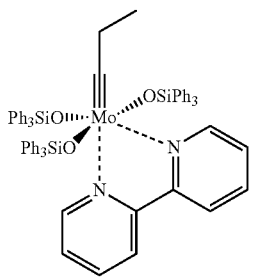
16b
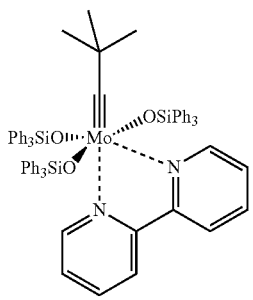
13e
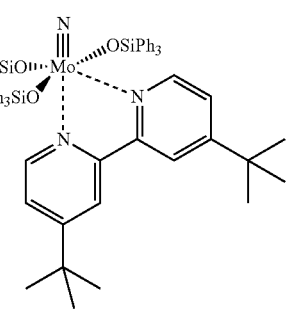
Likewise particularly preferred are compounds of the Formula 17a and 17b,
17a
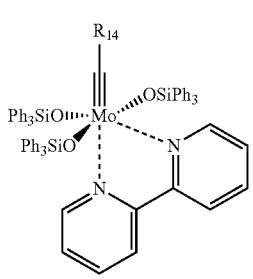
17b
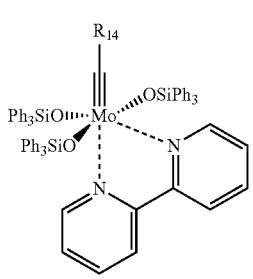
wherein
R$^{14}$ is a phenyl ring, which bears from 1 to 5 equal or different substituents selected from the list of: H, methyl, ethyl, propyl, butyl, tert.-butyl, isopropyl, phenyl, fluorine, chlorine, trifluoromethyl, methoxy, ethoxy, dimethylamino, diethylamino, trimethylsilyl.

Examples for particularly preferred compounds are the compounds 24a, 24b, 24c, 24d, 24e, 34a, which are described in more detail in section "Examples":

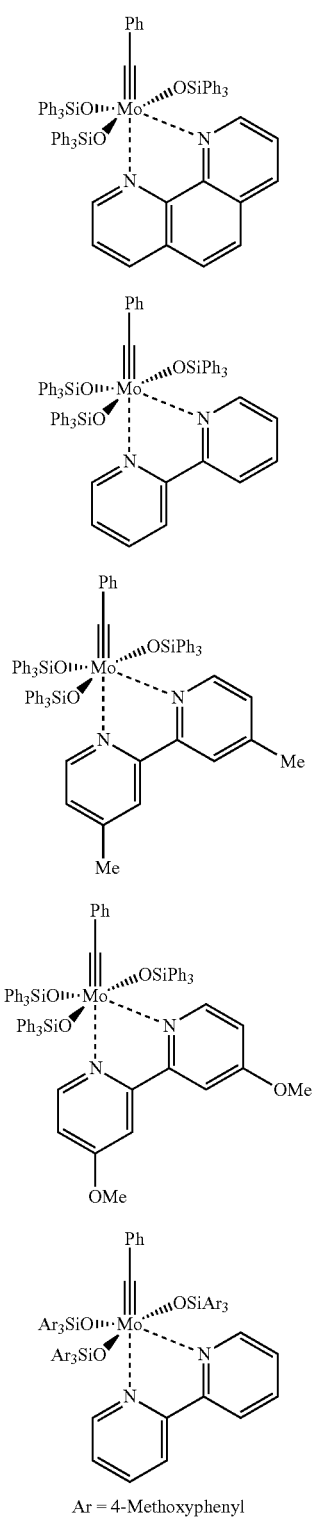

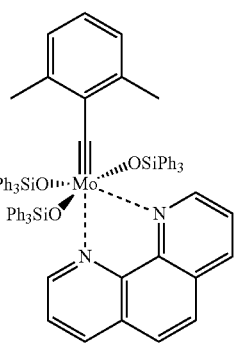

Another object of the present invention is a method for the preparation of compounds of the general Formula I

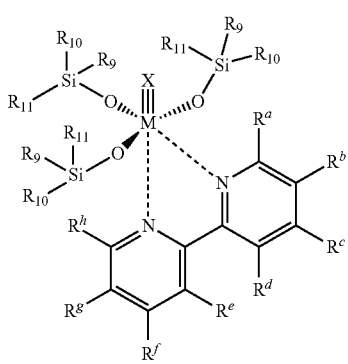

wherein
M, $R^a$, $R^b$, $R^c$, $R^d$, $R^e$, $R^f$, $R^g$, $R^9$, $R^{10}$, $R^{11}$ and X are defined as defined above.

in which a compound of the general Formula 18

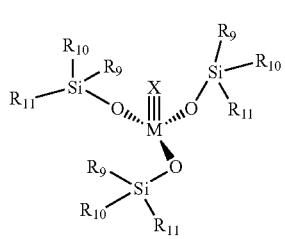

wherein
M, $R_9$, $R_{10}$, $R_{11}$ and X are defined as defined above,
is reacted with a compound of the general Formula 19

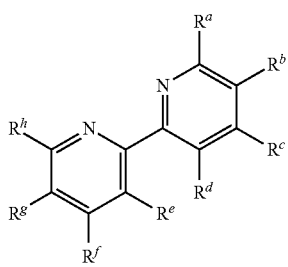

wherein $R^a$, $R^b$, $R^c$, $R^d$, $R^e$, $R^f$, $R^g$ and $R^h$ are defined as defined above.

The reaction of the compounds of Formula 18 with compounds of Formula 19 is carried out under inert gas (for example: nitrogen, argon) in an inert solvent at temperatures between −40° C. and +100° C., preferably at temperatures between 0° C. and 50° C. Preferred inert solvents are aromatic and aliphatic hydrocarbons, halogenated hydrocarbons or ethers; particularly preferred are pentanes, hexanes, heptanes, octanes, petroleum ether, benzene, toluene, xylenes, cumene, decalin, chlorobenzene, bromobenzene, fluorobenzene, trifluoromethylbenzene, dichlorobenzenes, trichlorobenzenes, dichloromethane, chloroform, tetrachloromethane, 1,2-dichloroethane, tetrahydrofuran, 1,4-dioxane, dimethoxyethane, diethyl ether, tert.-butylmethyl ether. Also mixtures of these solvents may be used.

Examples for the manufacture of compounds, which are particularly preferred according to the invention, are presented in Schemes 5 and 6 and in the examples. Thus, the particularly preferred nitrido complexes 13a, 13b, 13c, 13d can be obtained from the well accessible complex 20 (Chiu, H.-T. et al. Adv. Mater, 1998, 10, 1475) or from the corresponding halogeno complexes 21 (Close, M. R. et al., Inorg. Chem. 1994, 33, 4198; Geyer, A. M. et al. J. Am. Chem. Soc. 2008, 130, 8984) by reaction with Ph₃SiOH or Ph₃SiOM' (M'=Li, Na, K, Cs) and subsequent addition of a complexing ligand of the general Formula 19. In Scheme 5, the preparation of the corresponding complexes with 1,10-phenanthroline and 2,2'-bipyridine is presented, which are stable in solid form at air over several weeks.

Scheme 5. Nitrido complexes of tungsten and molybdenum with stabilizing phenanthroline or 2,2-bipyrdine ligands as well as representative preparation methods of such complexes.

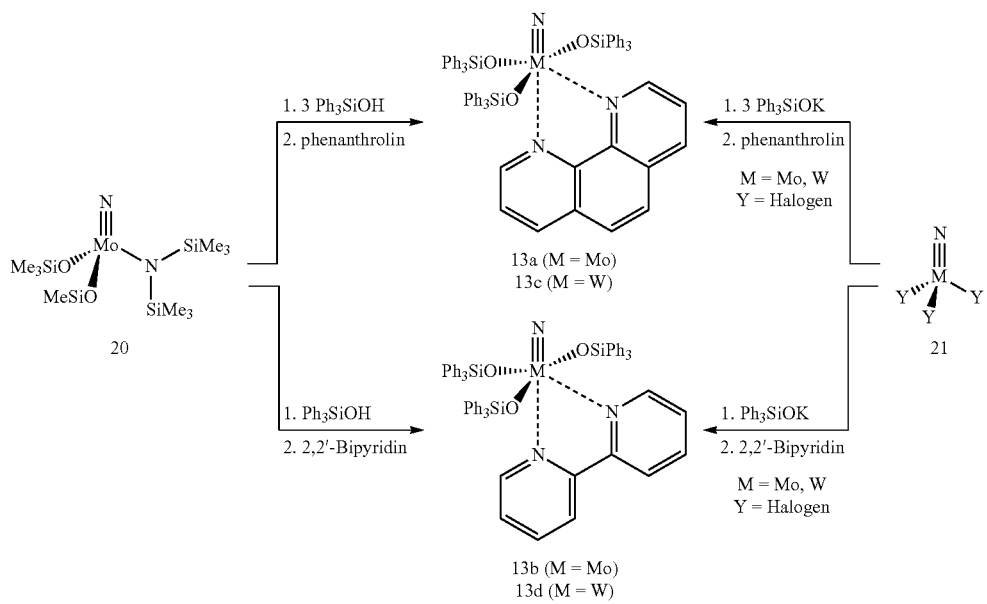

Analogously, the extremely air- and moisture-sensitive complex 23a may be converted by addition of ligands of the Formula 19 into the corresponding adducts. Exemplarily presented in Scheme 6 is the reaction with 1,10-phenanthroline and 2,2'-bipyridine by forming the particularly preferred complexes 24a and 24b, which are stable in solid form at air over several weeks.

Scheme 6. Examples of a preferred preparation method for particularly preferred adducts of Schrock-Alkylidyne complexes with stabilizing ligands; X = halogen.

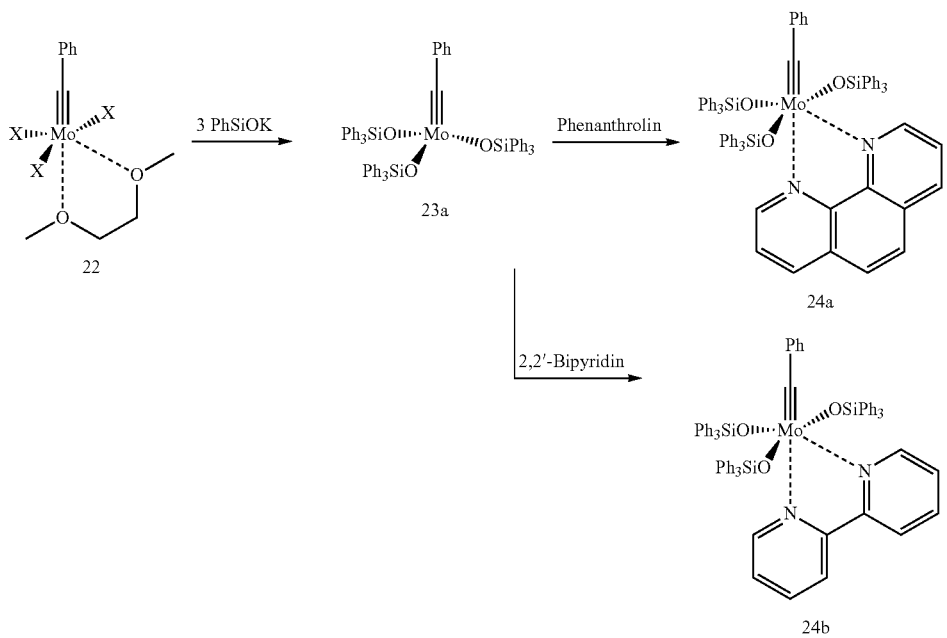

Complex 23a is novel and, amongst others, may be generated from known complexes of the type $X_3Mo\equiv CPh$ (X=Cl, Br) (Mayr, A. et al. *J. Am. Chem. Soc.* 1986, 108, 548; McCullough, L. G. et al., *J. Am. Chem. Soc.* 1985, 107, 5987; Stevenson, M. A. et al., *Organometallics* 1997, 16, 3572) by reaction with $Ph_3SiOM'$ (M'=Li, Na, K, Cs) in pure form or, preferred, in the form of adducts with a donor ligand such as acetonitrile, benzonitrile, pivalonitrile, tert.-butylmethyl ether, diethyl ether, diisopropyl ether, diphenyl ether, methoxybenzene, tetrahydrofuran, dioxane, dimethoxyethane.

It has been determined that complex 23a as well as its adducts with the mentioned donor ligands such as acetonitrile, benzonitrile, pivalonitrile, tert.-butylmethly ether, diethyl ether, diisopropyl ether, diphenyl ether, methoxybenzene, tetrahydrofuran, dioxane, dimethoxyethane provide for a high catalytic activity in the alkyne metathesis even at room temperature. Compared to this, the respective complexes 24a and 24b exhibit only a low catalytic activity under said conditions. As mentioned above and explained hereinunder, we have discovered that the catalytic activity can be recovered by addition of anhydrous metal salts or metal complexes as additives. Therefore, complexes 24a and 24b represent novel precatalysts for the alkyne metathesis.

Another object of the present invention are alkylidyne complexes of the general Formula 25 as well as the use thereof as catalysts for the alkyne metathesis,

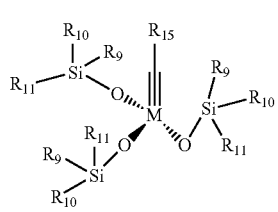

25 wherein

M=Mo, W, the substituents $R^9$, $R^{10}$, $R^{11}$ may be equal or may be different from one another and have the above-mentioned meaning, and $R^{15}$=$C_1$-$C_{12}$ alkyl, $C_3$-$C_{12}$ cycloalkyl, 6-18 membered aryl, 5-10 membered heteroaryl.

Likewise, a further object of the present invention are the adducts of the alkylidyne complexes of the general Formula 25 with donor solvents, which may be selected from the list: Acetonitrile, benzonitrile, pivalonitrile, diethyl ether, diisopropyl ether, tert.-butylmethyl ether, diphenyl ether, methoxybenzene, tetrahydrofuran, dioxane, dimethoxyethane, as well as the use as catalysts for the alkyne metathesis.

Preferred compounds of the general Formula 25 are such compounds in which $R^{15}$ is selected from the list: Methyl, ethyl, propyl, butyl, iso-propyl, tert.-butyl, trimethylsilylmethyl, benzyl, (dimethyl)(phenyl)methyl, phenyl, methylphenyl, dimethylphenyl, trimethylphenyl, methoxyphenyl, dimethoxyphenyl, fluorophenyl, pentafluorophenly, trifluoromethylphenyl, furyl.

In case the existence of compounds of Formula 25 has been postulated in the literature, such compounds, however, neither could be verified by isolation nor by means of spectroscopic methods. Therefore, compounds of Formula 25 are novel. We have discovered that these complexes as well as their adducts with donor solvents provide for high catalytic activity in alkyne metathesis reactions, for which reason these compounds are also an object of the present invention.

Particularly preferred are Schrock-Alkylidyne complexes of the general Formulas 23, 26, 27, 28, 29, 30, 34 as well as their adducts with acetonitrile, benzonitrile, pivalonitrile, tert.-butylmethyl ether, diethyl ether, diisopropyl ether, diphenyl ether, methoxybenzene, tetrahydrofuran, dioxane, dimethoxyethane,

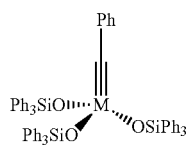

23

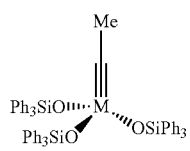

26

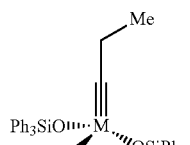

27

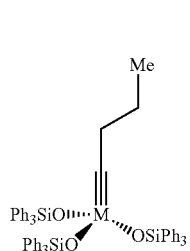

28

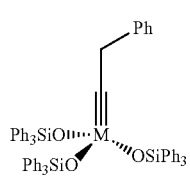

29

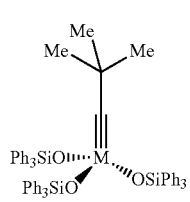

30

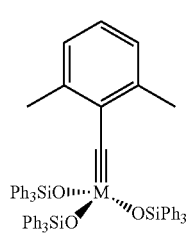

34 wherein M=Mo, W.

Particularly preferred are also complexes of the general Formula 31 as well as their adducts with acetonitrile, benzonitrile, pivalonitrile, tert.-butylmethyl ether, diethyl ether, diisopropyl ether, diphenyl ether, methoxybenzene, tetrahydrofuran, dioxane, dimethoxyethane,

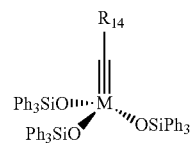

31 wherein
M=Mo, W
and $R^{14}$ is defined as defined above for complexes of the general Formula 17a and 17b.

Exemplarily for particularly preferred compounds are the complexes 23a ($Et_2O$), 30a (MeCN), 33 ($Et_2O$), which are described in more detail in the Examples:

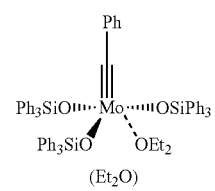

23a

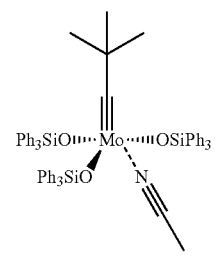

30a

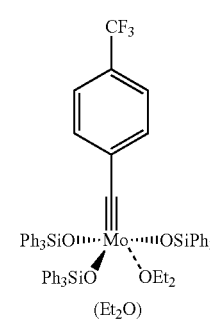

33

Also an object of the present invention is a method for carrying out alkyne metathesis reactions using a complex of the general Formulas I, 11, 11a, 12, 12,a, 17a, 17b or the complexes 13a, 13b, 13c, 13d, 13e, 14a, 14b, 15a, 15b, 16a, 16b, 24a, 24b, 24c, 24d, 24e or 34a as pre-catalysts. The method is characterized in that a solution or a suspension of the mentioned pre-catalysts is reacted in a suitable solvent with anhydrous metal salts or metal compounds as additives, which in turn may form stable complexes with the compounds of the general Formula 19, which are used as stabilizing ligands. In doing so, an activation of the complexes, which serve as pre-catalysts, occurs, probably by decomplexing the stabilizing ligand of the general Formula 19 from the respectively used pre-catalyst. The adducts of the ligand of the general Formula 19 with the added additive, which are formed in this reaction, may alternatively remain in the reaction mixture or may be separated off from the mixture prior to the alkyne metathesis. Basically, for this activation, all anhydrous metal salts or metal compounds may be used as additives, which form stable complexes with ligands of the general Formula 19. Examples for this new method for carrying out alkyne metathesis reactions are shown in Scheme 7 and are described in the section "Examples".

Preferred additives are: $MnY_2$, $FeY_2$, $FeY_3$, $CoY_2$, $CuY_2$, $ZnY_2$, $MgY_2$, $NiY_2$, $PdY_2$, $PtY_2$, $RuY_2$, $RuY_3$, $EuY_3$, wherein Y=F, Cl, Br, I, acetylacetonate, sulfate, sulfonate, nitrate, acetate, trifluoroacetate.

Particularly preferred additives are: $MnCl_2$, $FeCl_2$, $FeCl_3$, $CoCl_2$, $CuCl_2$, $ZnCl_2$.

Depending on the selected additive, the activation can be carried out at different temperatures, preferably at temperatures between −20° C. and +130° C., particularly preferred at temperatures between 20° C. and 100° C. All solvents may be used as solvents, which do not react with metal nitrides or metal alkylidynes; preferred solvents are hydrocarbons, halogenated hydrocarbons, and ethers; particularly preferred are pentanes, hexanes, heptanes, octanes, petroleum ether, benzene, toluene, xylenes, cumene, decalin, chlorobenzene, bromobenzene, fluorobenzene, trifluoromethylbenzene, dichlorobenzene, trichlorobenzene, dichloromethane, chloroform, tetrachloromethane, 1,2-dichloroethane, tetrahydrofuran, 1,4-dioxane, dimethoxyethane, diethyl ether, tert.-butylmethyl ether. Also mixtures of these solvents may be used.

Scheme 7. Representative example of the activation of a nitride complex of molybdenum with stabilizing phenanthroline ligand by ligand exchange with $MnCl_2$ as a preferred additive (Toluol has the meaning of toluene).

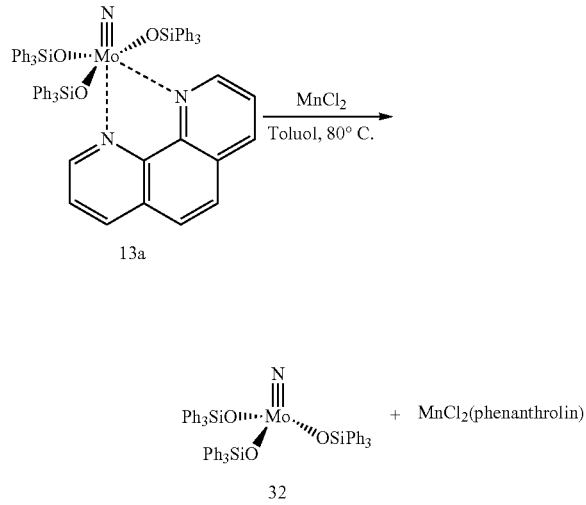

A further object of the present invention is a method for carrying out alkyne metathesis reactions in the course of which 2-butine is formed as one of the metathesis products, characterized in that the reaction is carried out in presence of molecular sieves as additives, which physically or chemically bind 2-butine.

The principle of the metathesis is depicted in Scheme 1, which already has been presented above:

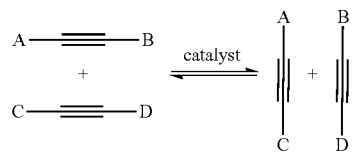

The following Schemes 8 and 9 show representative examples for alkyne metathesis reactions by release of 2-butine.

Scheme 8. Intermolecular alkyne metathesis reaction.

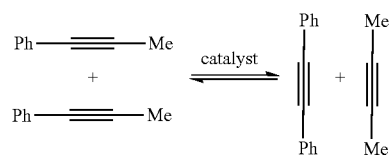

Scheme 9. Ring closure alkyne metathesis (RCAM) while forming 2-butine as a by-product.

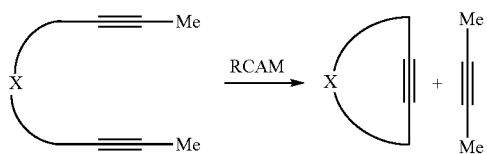

Surprisingly, we have discovered that the addition of a preferably dried molecular sieve (also denoted as mole sieve) effects an acceleration of the reaction and a considerable improvement of the yield. In doing so, the molecular sieve can be added in the form of pellets, rods, beads or as powder; preferred is the use of powders. Preferred is the use of molecular sieve 5 Ångström (MS 5 Å) as well as molecular sieve 4 Ångström (MS 4 Å).

Probably, the advantageous effect of the molecular sieve can be attributed to the absorption or adsorption of the 2-butine, wherein additionally effects cannot be ruled out. The amount of molecular sieve depends on the amount of the released 2-butine and can be varied in a broad range. Preferred is the use of 1-4 mg of molecular sieve per micromole of released 2-butine. The use of larger excesses of molecular sieve is possible.

FIG. 1 shows the comparison of the alkyne metathesis conversion of 1-propinylbenzene to tolane, wherein $Mo(\equiv CPh)(OSiPh_3)_3 \cdot OEt_2$ (23a.EtO$_2$) (1 mol %) at room temperature in toluene. The yields were determined by means of GC (versus biphenyl as internal standard). The curve under "addition of molecular sieve 5 Å" relates to the use of powdered MS 5 Å (2 mg per pmol of released 2-butine). As is shown in FIG. 1 for the example of an alkyne metathesis reaction, which is catalyzed by complex 23a, high conversions can be reached in this manner even at room temperature, which cannot be reached in absence of molecular sieve while employing the same conditions.

The effect of the molecular sieve that is described in this invention cannot be attributed to the removal of water traces from the reaction mixture. Thus, the present invention basically differs from methods for carrying out alkyne metathesis reactions, in which MS 4 Å is used in order to bind moisture in the reaction mixture (Huc, V. et al. *New J. Chem.* 2003, 27, 1412). In this case, the use of MS 4 Å merely leads to results, which are also achieved when using dried and distilled solvents in absence of MS 4 Å (Maraval, V. et al. *Tetrahedron Lett.* 2006, 47, 2155). The fact that the effect of the molecular sieve, which is described in the present invention, which leads to an increase of the reaction rate as well as to an improvement of the conversion, is not attributed to the removal of water traces, may also be derived therefrom that the use of molecular sieve 3 Å has no important effect on the conversion of 1-propinylbenzene to tolane. In fact, molecular sieve 3 Å binds moisture, however, may not efficiently bind hydrocarbons having 4 carbon atoms such as 2-butine.

The increase of the reaction rate of alkyne metathesis reactions as well as the improvement of the conversion and the thus achievable yield of the respective reaction products, which is effected according to the invention by adding molecular sieve, thus, probably, is based on the removal of the 2-butine from the reaction mixture, which is otherwise present in the equilibrium.

The removal of the resulting 2-butine from the reaction mixture is typically achieved thereby that the reactions are carried out at increased temperature and/or at low pressure (Fürstner, A. et al., *Angew. Chem.,* 1998, 110, 1758; Beer, S. et al. *Organometallics* 2009, 28, 1534). Alternative methods for the improvement of the conversion in alkyne metathesis reactions are based until now on the avoidance of 2-butine as by-product: Using modified substrates, alkynes may be formed instead of 2-butine, which precipitate from the reaction mixture (precipitation method) (Zhang, W. *Org. Synth.* 2007, 84, 163; Zhang, W. et al. *J. Am. Chem. Soc.* 2004, 126, 12796). The substrates, which are used for this, however, have to be costly manufactured in several steps, and are also not ideal in view of the atom economy. By means of the present invention, the manufacture of such particular substrates can be avoided. Likewise, also by adding molecular sieve, preferably MS 4 Å or MS 5 Å, alkyne metathesis reaction can be carried out without increased temperatures and/or applying vacuum.

The effect of molecular sieve on alkyne metathesis reactions, in the course of which 2-butine is formed as one of the metathesis products, is independent from the used pre-catalyst or catalyst. Preferred is the use of molecular sieves, in particular of MS 4 Å or MS 5 Å, in combination with one of the pre-catalysts, which are mentioned in the present invention, or catalysts for carrying out alkyne metathesis reactions.

Likewise preferred is the use of molecular sieves, in particular of MS 4 Å or MS 5 Å, in combination with one of the following pre-catalysts or catalysts for carrying out alkyne metathesis reactions: 1 (Listemann, M. L. et al. *Organometallics* 1985, 4, 74), 2 (Beer, S. et al. *Organometallics* 2009, 29, 1534), 3 (Zhang, W. *Org. Synth.* 2007, 84, 163), 4 (Fürstner, A. et al. *J. Am. Chem. Soc.* 1999, 121, 9453), 5 (Geyer, A. M. et al. *J. Am. Chem. Soc.* 2008, 130, 8984), 6 (Geyer, A. M. et al. *J. Am. Chem. Soc.* 2008, 130, 8984), 9 (Fürstner et al., *J. Am. Chem. Soc.* 2009, 131, 9468).

Examples for the preparation of claimed catalysts and pre-catalysts as well as the carrying out of alkyne metathesis reactions according to the present invention are summarized in Tables 1-3 and in section "Examples".

TABLE 1

Intermolecular alkyne metathesis reactions

| Substrate | Product | | 13a [a] | 13b [a] | 23a• Et$_2$O [b] | 24a [c] | 24b [c] |
|---|---|---|---|---|---|---|---|
| (2-R-phenyl)-C≡CH | bis(2-R-phenyl)acetylene | R = H | 93-99% | 99% | 99% | 99% | 99% |
| | | R = OMe | 96% | 94% | 97% | 97% | 97% |
| | | R = SMe | 87% | 96% | 98%[d] | 96%[d] | 95%[d] |
| | | R = COOMe | | | | 92% | 94% |
| F$_3$C-C$_6$H$_4$-C≡CH | F$_3$C-C$_6$H$_4$-C≡C-C$_6$H$_4$-CF$_3$ | | | 93% | 93% | | 94% |
| NC-C$_6$H$_4$-C≡CH | NC-C$_6$H$_4$-C≡C-C$_6$H$_4$-CN | | | | | | 94% |
| O$_2$N-C$_6$H$_4$-C≡CH | O$_2$N-C$_6$H$_4$-C≡C-C$_6$H$_4$-NO$_2$ | | | | | | 69% |
| 3-pyridyl-C≡CH | bis(3-pyridyl)acetylene | | 85%[e] | | 90%[d] | 86%[d] | |
| 2-thienyl-C≡CH | bis(2-thienyl)acetylene | | 96% | 93% | 88% | 87% | 90% |

TABLE 1-continued

Intermolecular alkyne metathesis reactions

| Substrate | Product | 13a [a] | 13b [a] | 23a•Et$_2$O [b] | 24a [c] | 24b [c] |
|---|---|---|---|---|---|---|
| TsO–⎯≡⎯ | TsO–⎯≡⎯–OTs | | | 92% | 92% | |
| MeOOC–⎯≡⎯ | MeOOC–⎯≡⎯–COOMe | 83% | 89% | 91% | 92% | |
| (bicyclic ketone with butynyl group) | (bis-coupled bicyclic ketone) | | | 92% | 88% | |
| (3-cyanophenoxy-dodecyne) | (bis(3-cyanophenoxy) product) | 81% | 87% | 89% | 89% | |

[a] 13a or 13b (10 mol %), MnCl$_2$ (10 mol %), MS 5 Å, toluene, 80-100° C.
[b] 23a•Et$_2$O (2 mol %), toluene, room temperature, MS 5 Å
[c] 24a or 24b (5 mol %, MnCl$_2$ (5 mol %), toluene, 80-100° C., 30 min; then addition of the substrate and reaction at room temperature
[d] at 50° C.
[e] at 100° C.

TABLE 2

Intermolecular alkyne metathesis reactions

| Substrate | Product | 13a [a] | 13b [d] | 23a•Et$_2$O [b] | 24a [c] | 24b [c] |
|---|---|---|---|---|---|---|
| (phthalate diester with two terminal propynyl chains) | (macrocyclic phthalate diyne) | | 69% | 97% | 94% | 90% |
| (4-nitrophthalate diester with longer alkynyl chains) | (macrocyclic nitrophthalate diyne) | | | | 85% | |

TABLE 2-continued

Intermolecular alkyne metathesis reactions

| Substrate | Product | 13a [a] | 13b [d] | 23a· Et₂O [b] | 24a [c] | 24b [c] |
|---|---|---|---|---|---|---|
| (diyne diester, succinate) | (macrocyclic alkyne lactone) | 60% | 81% | 73% | 78% | 81% |
| (diyne diester, pimelate) | (macrocyclic alkyne lactone) | | 86% | 92% | | 91% |
| (diyne ester with NFmoc side chain) | (macrocyclic alkyne with NFmoc) | | | 90% | | |
| (epothilone precursor diyne, R = TBS) | (epothilone macrocycle, R = TBS) | | | 91% | | |
| (3,6-diethynyl-N-tetradecylcarbazole) | (cyclic tetracarbazole-ethynylene) | 80% | 82% | | | 82% |

[a] 13a (10 mol %), MnCl₂ (10 mol %), MS 5 Å, toluene, 80-100° C.
[b] 23a·Et₂O (2 mol %), toluene, room temperature, MS 5 Å
[c] 24a (5 mol %), MnCl₂ (5 mol %), toluene, 80-100° C., 30 min; then addition of the substrate, MS 5 Å and carrying out the alkyne metathesis reaction at room temperature
[d] 13b (10 mol %), MnCl₂ (10 mol %), toluene, 80-100° C., without addition of MS 5 Å

TABLE 3

Alkyne cross-metathesis reactions

| Substrates | | Product | 13a [a] | 23a•Et$_2$O [b] | 24b [c] |
|---|---|---|---|---|---|
| [pyridine-C≡CH] | 5-decine | [pyridine-C≡C-Bu] | | 65% | 75% |
| [EtO-C(O)-CH=CH-C≡C-Me] | tolane | [EtO-C(O)-CH=CH-C≡C-Ph] | | 62% | |
| [EtO-C(O)-C≡C-Me] | 5-decine | [EtO-C(O)-C≡C-Bu] | | | |
| [Ph-CH$_2$CH$_2$-CH(OTBDPS)-CH$_2$-C≡C-Me] | tolane | [Ph-CH$_2$CH$_2$-CH(OTBDPS)-CH$_2$-C≡C-Ph] | 60% | | 71% |

[a] 13a (10 mol %), MnCl$_2$ (10 mol %), toluene, 80-100° C., without MS 5 Å.
[b] 23a•Et$_2$O (2 cat.), toluene, room temperature, MS 5 Å.
[c] 24b (5 mol %), MnCl$_2$ (5 mol %), toluene, 80-100° C., 30 min; then addition of the substrate, MS 5 Å and carrying out the alkyne metathesis reaction at room temperature

EXAMPLES

Abbreviations: phen=1,10-phenanthroline; bipy=2,2'-bipyrdine; Ts=tosyl; TMS=trimethylsilyl; TBS=tert.-butyldimethylsilyl; TBDPS=tert.-butyldiphenylsilyl; THP=tetrahydropyranyl; Fmoc=9-fluorenylmethoxycarbonyl; dme=1,2-dimethoxyethane The molecular sieves used for carrying out the alkyne metathesis reactions were activated by heating to at least 200° C. in vacuo and were stored under argon.

I. Preparation and Use of Preferred Catalysts and Phenanthroline Adducts Derived Therefrom

1. Preparation of Mo(≡N)(OSiPh$_3$)$_3$·phen (13a)

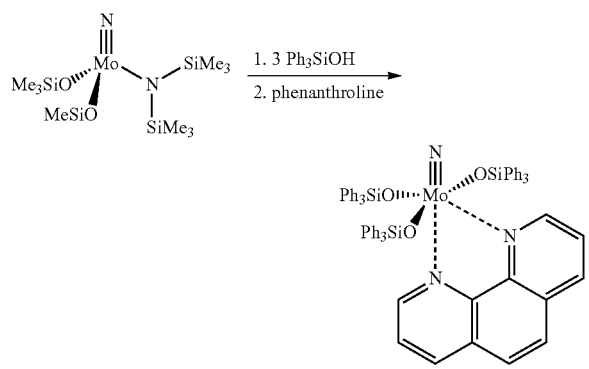

Figure 2:
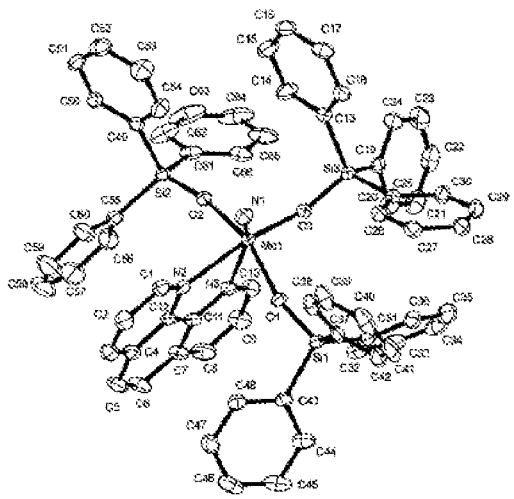

In a dried 500 mL Schlenk-tube, which has been flooded with argon, [Mo(≡N)(OTMS)$_2$(N(TMS)$_2$)] (8.97 g, 20.0 mmol) was provided and was dissolved in 200 mL of dried toluene. Ph$_3$SiOH (16.58 g, 60.0 mmol) was added in argon counter-flow, and the obtained yellowish solution was stirred for 30 min at room temperature. The solution was transferred to a 1 L Schlenk-tube, which already contained 1,10-phenanthroline (doubly sublimated, 3.60 g, 20.0 mmol). After few minutes, the obtained reaction mixture changed to a clear yellowish solution, some minutes later a light yellow precipitation was slowly formed. The solvent was removed after 30 min and the obtained residue was dried for one hour at room temperature in high vacuum ($10^{-3}$ mbar) and for one hour at 60° C. in high vacuum (approximately $10^{-3}$ mbar). The thus obtained yellow solid was re-crystallized triply from hot toluene. For this, the solid was at first dissolved in 500 mL of hot toluene (105° C.), a remaining insoluble residue was removed by filtration of the hot solution. The solution was slowly cooled down to room temperature and was left for two days. Subsequently, the green solution was decanted and the crystals were dried in vacuo. The mother liquor was concentrated at room temperature to dryness, and the before-described procedure was repeated with 200 mL of toluene. Further 2.95 g of product were obtained. A third crystallization with 100 mL of toluene resulted in further 1.59 g of product. In total, 18.98 g of [Mo(≡N)(OSiPh$_3$)$_3$(phen)] in the form of yellow crystals were obtained. Depending on the degree of dryness, the solid may contain varying amounts of toluene. This complex can be stored over months at air without recognizable decomposition. $^1$H NMR (400 MHz, CD$_2$Cl$_2$): δ=9.20 (dd, J=5.0, 1.6 Hz, 1H), 8.98 (dd, J=4.5, 1.6 Hz, 1H), 8.24 (dd, J=8.2, 1.6 Hz, 1H), 7.89-7.85 (m, 6H), 7.83 (dd, J=8.2, 1.6 Hz, 1H), 7.67 (d, J=8.9 Hz, 1H), 7.59 (dd, J=8.2, 4.5 Hz, 1H), 7.46 (d, J=8.9 Hz, 1H), 7.31-7.25 (m, 3H), 7.14-7.10 (m, 6H), 7.10-7.05 (m, 18H), 6.98 (dd, J=8.1, 5.0 Hz, 1H), 6.91-6.85 (m, 12H); $^{13}$C NMR (100 MHz, CD$_2$Cl$_2$): δ=156.2, 147.7, 142.2, 141.5, 139.0, 138.0, 137.7, 137.2, 136.1, 135.2, 134.9, 129.6, 129.5, 129.0, 128.3, 127.9, 127.6, 127.4, 127.1, 127.1, 124.3, 124.2; IR (ATR): 3044, 3021, 1588, 1518, 1495, 1483, 1426, 1341, 1298, 1262, 1222, 1188, 1113, 1104, 1056, 1028, 1011, 998, 942, 893, 865, 840, 768, 740, 727, 708, 697 cm[1]; MS (ESI[+]): m/z (%): 1118 (100 [M+H[+]], 1043 (10); HRMS (ESI[+]): m/z: calculated for $C_{66}H_{54}MoN_3O_3Si_3$ [M+H[+]]: 1118.2513, found: 1118.2523. The structure of [Mo(≡N)(OSiPh$_3$)$_3$(phen)] was confirmed by crystal structure analysis (FIG. 2).

2. Preparation of Mo(≡CPh)(OSiPh$_3$)$_3$·OEt$_2$ (23a.Et$_2$O)

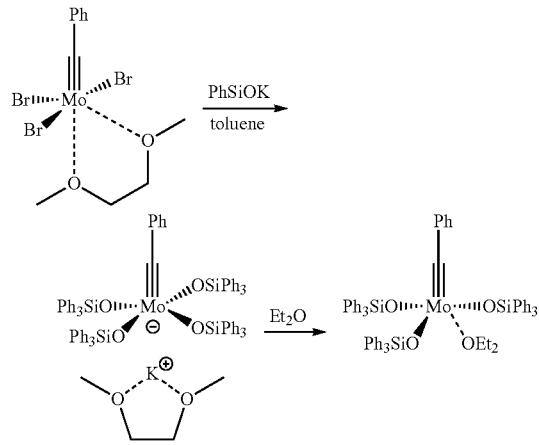

In a dried 100 mL Schlenk-tube, which has been flooded with argon, Mo(≡CPh)Br$_3$(dme) (472 mg, 0.92 mmol) was dissolved in 100 mL of toluene and was treated with a solution of Ph$_3$SiOK (925 mg, 2.94 mmol) in 10 mL of toluene. After one hour at room temperature, it was filtered and the solvent was removed in vacuo. The residue was treated with 10 mL of diethyl ether, wherein a mauve solid precipitated. After washing with 10 mL of diethyl ether and drying in vacuo, Mo(≡CPh)(OSiPh$_3$)$_3$OEt$_2$ was obtained as a mauve solid (751 mg, 75%). $^1$H NMR (400 MHz, [D$_8$]-toluene): δ (ppm)=7.71 (dd, J=8.0, 1.3 Hz, 18H); 7.08 (tt, J=7.4, 1.4 Hz, 9H); 6.93 (t, J=7.6 Hz, 18H); 6.84 (t, J=7.7 Hz, 2H); 6.68 (tt, J=7.4, 1.2 Hz, 1H); 6.56 (d, J=7.6 Hz, 2H); 3.29 (q, J=7.0 Hz, 4H); 1.12 (t, J=7.0 Hz, 6H); [13]NMR (100 MHz, [D$_8$]-toluene): δ (ppm)=282.6, 145.7, 140.4, 138.2, 137.4, 131.2, 130.8, 129.7, 128.8, 128.4, 128.1, 127.5, 126.3, 66.6, 16.2.

3. Preparation of Mo(≡CC$_6$H$_4$CF$_3$)(OSiPh$_3$)$_3$·OEt$_2$ (33.Et$_2$O)

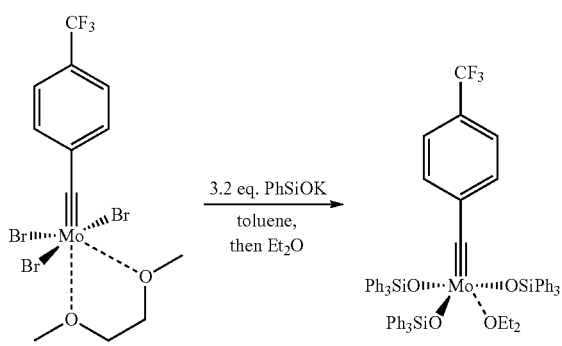

The preparation was carried out analogously to the above recipe. The complex showed the following characteristic NMR signal: $^{19}$F-NMR (300 MHz, [D$_8$]-toluene: δ (ppm)= −62.8 (s).

4. Preparation of Mo(≡CtBu)(OSiPh$_3$)$_3$(MeCN) (30.MeCN)

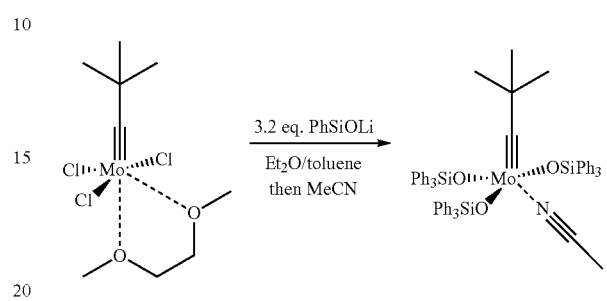

The complex was analogously prepared to the above recipe, wherein during the processing acetonitrile was used instead of diethyl ether. Characteristic data: $^1$H-NMR (300 MHz, [D$_8$]-toluene): δ (ppm)=7.83 (dd, J=7.7, 1.3 Hz, 18H), 7.21-7.10 m, 27H), 0.56 (s, 3H), 0.38 (s, 9H); $^{13}$C-NMR (75 MHz, [D$_8$]-toluene): δ(ppm)=323.5, 136.9, 135.9, 130.1, 128.2, 127.9, 54.9, 29.4, 1.4.

Figure 3:
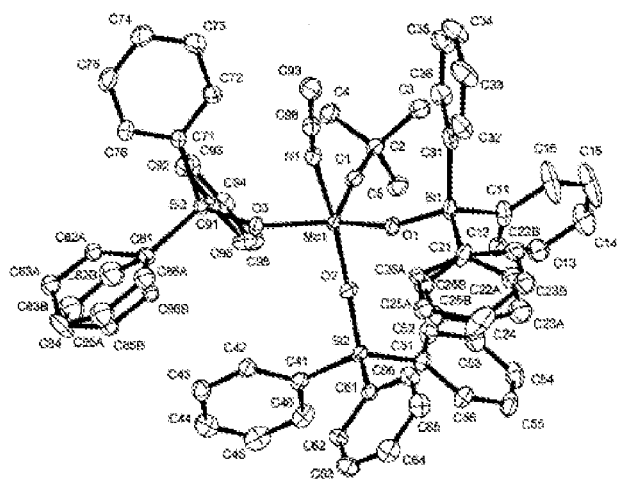

The structure of complex 30.MeCN was confirmed by crystal structure analysis (FIG. 3).

5. Preparation of Mo(≡CPh)(OSiPh$_3$)$_3$(phen) (24a)

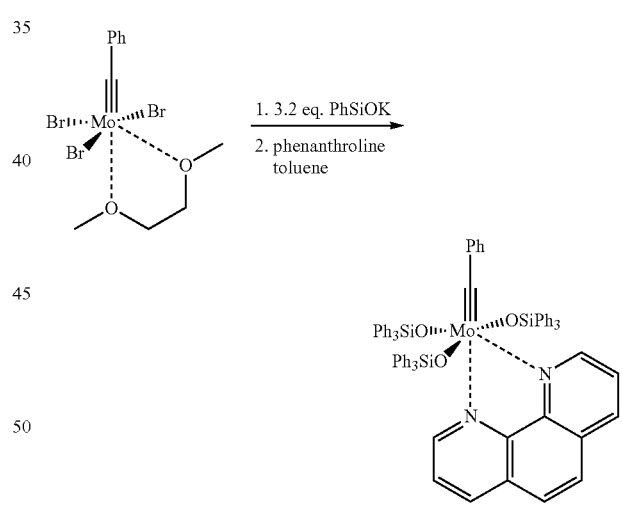

In a dry 100 mL Schlenk-tube, which has been flooded with argon, Mo(≡CPh)Br$_3$(dme) (492 mg, 0.96 mmol) was dissolved in 15 mL of toluene and was treated with a solution of Ph$_3$SiOK (962 mg, 3.06 mmol) in 15 mL of toluene. After one hour at room temperature, it was filtered and the filtrate was dropped to a solution of phenanthroline (156 mg, 0.86 mmol) in 5 mL of toluene, wherein an intensive violet color occurs; the solution appears nearly black with increasing concentration. After one hour at room temperature, the reaction mixture was left over night for crystallization. The solid was washed twice with 10 mL of diethyl ether, respectively. After drying in high vacuum, Mo(≡CPh)(OSiPh$_3$)$_3$(phen) was obtained as a violet solid (483 mg, 43%). $^1$H NMR (400 MHz, CD$_2$Cl$_2$): δ(ppm)=9.26 (dd, J=4.6, 1.6 Hz, 1H), 9.14 (dd, J=4.3, 1.8 Hz, 1H), 8.90 (dd, J=5.0, 1.8 Hz, 1H), 8.33 (dd, J=8.2, 1.6 Hz, 1H), 8.30 (dd, J=8.1, 1.8 Hz, 1H), 7.89 (dd, J=8.0, 1.3 Hz, 3H), 7.82 (dd, J=8.2, 1.5 Hz, 1H), 7.74 (d, J=8.8 Hz, 1H), 7.66-7.58 (m, 2H), 7.53 (d, J=8.8 Hz, 1H), 7.49-7.43 (m, 6H), 7.41-7.37 (m, 4H), 7.28 (tt, J=7.6, 1.3 Hz, 5H), 7.19 (tt, J=7.4, 1.4 Hz, 2H), 7.06 (tt, J=7.4, 1.3 Hz, 4H), 7.03 (dd, J=8.0, 1.4 Hz, 8H), 6.96-6.92 (m, 5H), 6.86 (tt, J=7.4, 1.2 Hz, 1H), 6.80 (t, J=7.9, 8H), 6.31 (dd, J=8.4, 1.4 Hz, 2H). $^{13}$C NMR (100 MHz, CD$_2$Cl$_2$): δ(ppm)=142.7, 139.4, 136.2, 135.8, 135.5, 135.3, 135.2, 131.2, 130.2, 129.2, 128.6, 128.3, 128.1, 127.7, 127.3, 127.2, 127.0; the alkilidyne carbon could not be detected; IR (film): 3065, 3047, 3022, 1958, 1895, 1823, 1649, 1625, 1587, 1566, 1516, 1483, 1427, 1381, 1342, 1302, 1260, 1221, 1186, 1141, 1110, 1031, 1017, 998, 927, 867, 836, 754, 739, 725, 696 cm$^{-1}$.

Figure 4:
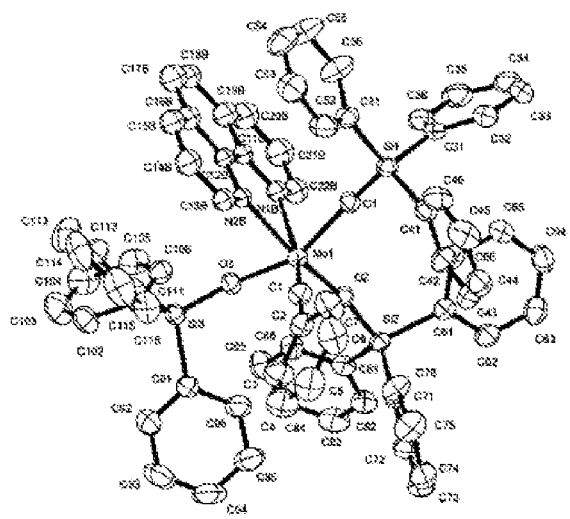

The structure of complex 24a was confirmed by crystal structure analysis (FIG. 4).

6. Preparation of W(≡CPh)(OSiPh$_3$)$_3$.(phen)

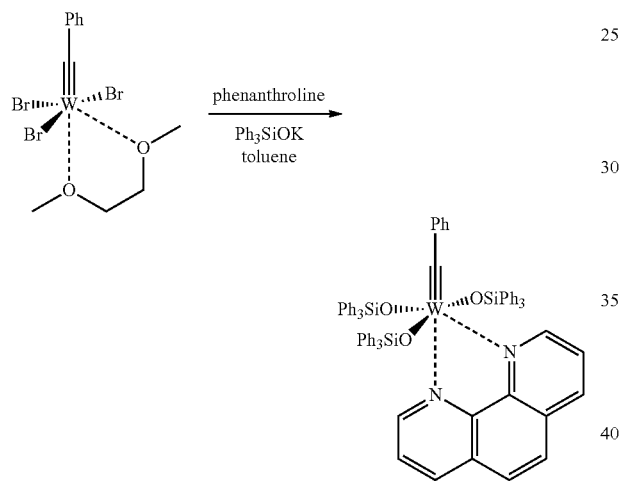

In a dry 25 mL Schlenk-tube, which has been flooded with argon, [W(≡CPh)Br$_3$.(dme)] (349 mg, 0.58 mmol) was dissolved in toluene (3 mL) and was treated with a solution of phenanthroline (104 mg, 0.58 mmol) in toluene (2 mL). After one hour at room temperature, a solution of Ph$_3$SiOK (546 mg, 1.74 mmol) was added in toluene (5 mL), and the mixture was stirred for 1 h at 80° C. Subsequently, the solvent was removed in vacuo, and the residue was washed with diethyl ether (20 mL). The obtained solid was dissolved in dichloromethane (5 mL) and the product was precipitated with pentane (25 mL). After washing the filtered solid with pentane (5 mL) and drying in vacuo, [W(≡CPh)(OSiPh$_3$)$_3$(phen)] was obtained as red-brown solid (158 mg, 21%). $^1$H NMR (400 MHz, CD$_2$Cl$_2$): δ=9.35 (dd, J=5.1, 1.6 Hz, 1H), 9.27 (dd, J=4.6, 1.6 Hz, 1H), 8.34 (dd, J=8.2, 1.5 Hz, 1H), 7.92 (dd, J=8.0, 1.4 Hz, 6H), 7.86 (dd, J=8.3, 1.5 Hz, 1H), 7.73 (d, J=8.8 Hz, 1H), 7.60 (dd, J=8.2, 4.6 Hz, 1H), 7.52 (d, J=8.9 Hz, 1H), 7.21 (tt, J=7.5, 1.4 Hz, 3H), 7.14-7.03 (m, 20H), 6.96 (t, J=7.7 Hz, 6H), 6.89 (dd, J=8.2, 5.1 Hz, 1H), 6.80 (t, J=7.7 Hz, 12H), 6.58 (tt, J=7.4, 1.2 Hz, 1H), 6.21 (dd, J=8.3, 1.2 Hz, 2H); $^{13}$C NMR (100 MHz, CD$_2$Cl$_2$): δ=281.7, 158.1, 147.3, 145.5, 143.6, 143.2, 139.0, 138.5, 138.4, 137.7, 136.3, 135.7, 135.3, 135.0, 134.8, 130.3, 129.9, 129.3, 128.7, 128.3, 127.8, 127.7, 127.5, 127.3, 127.2, 126.3, 125.6, 124.9, 124.1; IR (film, cm$^{-1}$): 3047, 2996, 1585, 1516, 1485, 1426, 1260, 1110, 1017, 999, 932, 836, 739, 695.

Figure 5:
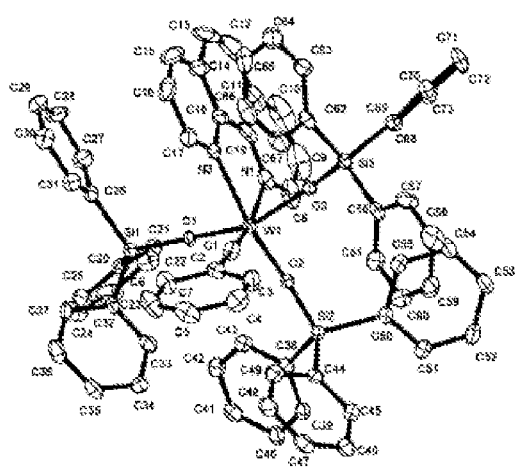

The crystal structure of [W(≡Ar)(OSiPh$_3$)$_3$(phen)] is presented in FIG. 5.

7. Preparation of Mo(≡CAr)(OSiPh$_3$)$_3$ Wherein Ar=2,6-dimethylphenyl (34)

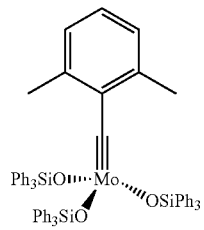

In a dry 25 mL Schlenk-tube, which has been flooded with argon, [Mo(≡CAr)Br$_3$.(dme)] (243 mg, 448 μmol) was dissolved in toluene (3 mL) and was treated with a solution of Ph$_3$SiOK (422 mg, 1.34 mmol) in toluene (2 mL). After one hour at room temperature, it was filtered and the filtrate was concentrated. The residue was crystallized from pentane (25 mL). After drying in vacuo, [Mo(≡CAr)(OSiPh$_3$)$_3$] was obtained as yellow solid (289 mg, 62%). $^1$H NMR (400 MHz, CD$_2$Cl$_2$): δ=7.56 (d, J=7.2 Hz, 18H), 7.36 (t, J=7.8 Hz, 9H), 7.21 (t, J=7.4 Hz, 18H), 6.64 (t, J=7.6 Hz, 1H), 6.55 (dd, J=7.6, 0.6 Hz, 2H), 1.71 (s, 6H); $^{13}$C NMR (100 MHz, CD$_2$Cl$_2$): δ=307.3, 144.7, 139.6, 136.5, 136.0, 136.7, 135.8, 135.5, 135.4, 135.2, 130.5, 130.3, 129.8, 128.7, 128.3, 128.1, 127.7, 127.2, 126.1, 20.2.

Figure 6:
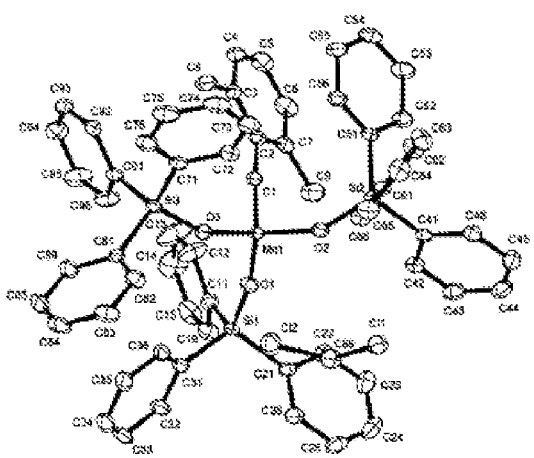

The crystal structure of Mo(≡CAr)(OSiPh$_3$)$_3$, wherein AR=2,6-dimethylphenyl, is presented in FIG. 6.

8. Preparation of [Mo(≡CAr)(OSiPh$_3$)$_3$.(phen)] wherein Ar=2,6-dimethylphenyl (34a)

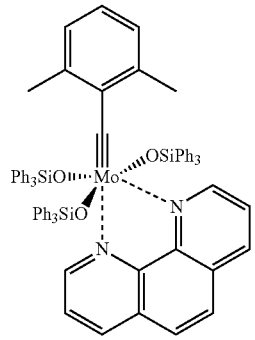

In a dry 25 mL Schlenk-tube, which has been flooded with argon, [Mo(≡CAr)Br$_3$.(dme)] (89 mg, 164 μmol) was dissolved in toluene (3 mL) and was treated with a solution of Ph$_3$SiOK (206 mg, 656 mmol). After one hour at room temperature, it was filtered and a solution of phenanthroline (29 mg, 164 mmol) in toluene (1 mL) was added to the filtrate. Subsequently, it was stirred for one hour at room temperature prior to the removal of the solvent in vacuo. The residue was washed with diethyl ether (5 mL), dissolved in dichloromethane (1 mL), and the product was precipitated by means of pentane (5 mL). After washing the precipitate with pentane (5 mL) and drying in vacuo, [Mo(≡CAr)(OSiPh₃)₃(phen)] was obtained as green solid (146 mg, 73%). IR (film, cm⁻¹): 3048, 2995, 1588, 1515, 1482, 1426, 1262, 1110, 1017, 999, 932, 836, 739, 695. ¹H NMR (400 MHz, CD₂Cl₂): δ=9.38 (dd, J=5.1, 1.6 Hz, 1H), 8.86 (dd, J=4.6, 1.6 Hz, 1H), 7.99 (dd, J=8.2, 1.6 Hz, 1H), 7.92 (dd, J=8.2, 1.6 Hz, 1H), 7.89 (dd, J=8.0, 1.4 Hz, 6H), 7.59 (d, J=8.8 Hz, 1H), 7.55 (d, J=8.8 Hz, 1H), 7.21 (tt, J=7.5, 1.4 Hz, 3H), 7.18 (dd, J=8.2, 5.0 Hz, 1H), 7.14 (dd, J=8.2, 4.6 Hz, 1H), 7.06-6.99 (m, 12H), 6.85-6.72 (m, 27H), 2.30 (s, 6H); ¹³C NMR (100 MHz, CD₂Cl₂): δ=297.9, 156.4, 148.0, 143.4, 142.9, 142.6, 142.4, 139.1, 138.9, 138.8, 137.2, 136.4, 135.5, 135.3, 130.5, 130.3, 130.1, 129.9, 128.4, 128.3, 128.1, 127.7, 127.6, 127.1, 127.0, 126.8, 126.4, 124.2, 124.1, 21.4.

Figure 7:
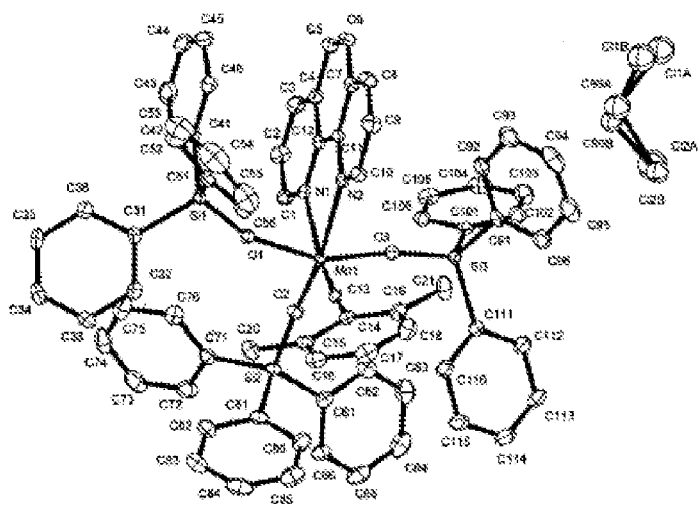

The crystal structure of [Mo(≡CAr)(OSiPh₃)₃.(phen)], wherein AR=2,6-dimethylphenyl, is presented in FIG. 7. The crystal contains co-crystallized CH₂Cl₂.

9. Alkyne Ring-Closure Metathesis Using [Mo(≡N)(OSiPh₃)₃.(Phen)]

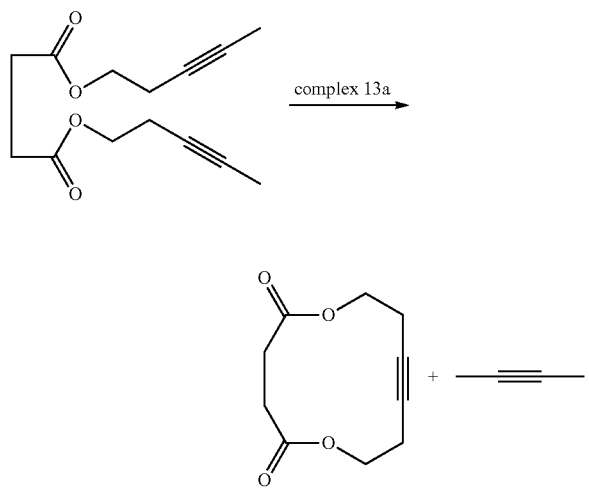

In a dry 500 mL Schlenk-tube, which has been flooded with argon, succinic acid dipent-3-inyl ester (5.00 mmol, 1.251 g), [Mo(≡N)(OSiPh₃)₃(phen)].0.5 toluene (0.500 mmol, 581.2 mg), MnCl₂ (0.500 mmol, 62.9 mg) and molecular sieve (10.0 g, 5 Å, powder) were suspended in 250 mL of toluene. The reaction solution was stirred for 24 h at 80° C. and was filtered after cooling over a short silica gel column. The filtrate was concentrated and the residue was purified by means of column chromatography (hexane/EtOAc 4:1). 1,6-dioxacyclododec-9-in-2,5-dione was isolated as colorless oil (yield 60%). ¹H NMR (400 MHz, CD₂Cl₂): δ=4.21-4.14 (m, 4H), 2.61 (s, 4H), 2.44-2.37 (m, 4H); ¹³C NMR (100 MHz, CD₂Cl₂): δ=171.9 (2×C), 79.0 (2×C), 61.6 (2×CH₂), 30.2 (2×CH₂), 19.7 (2×CH₂); IR (film): ν=2965, 2915, 2840, 1729, 1458, 1421, 1383, 1353, 1336, 1267, 1251, 1158, 1053, 1030, 1000, 952, 837 cm⁻¹; MS (EI) m/z (%): 166 (1), 101 (14), 78 (100), 66 (59), 65 (16), 55 (7), 40 (12), 28 (7); HRMS (ESI): m/z: calculated for C₁₀H₁₂O₄+Na: 219.0628; found: 219.0627.

10. Alkyne Ring-Closure Metathesis Using [Mo(≡CPh)(OSiPh₃)₃(Et₂O)]

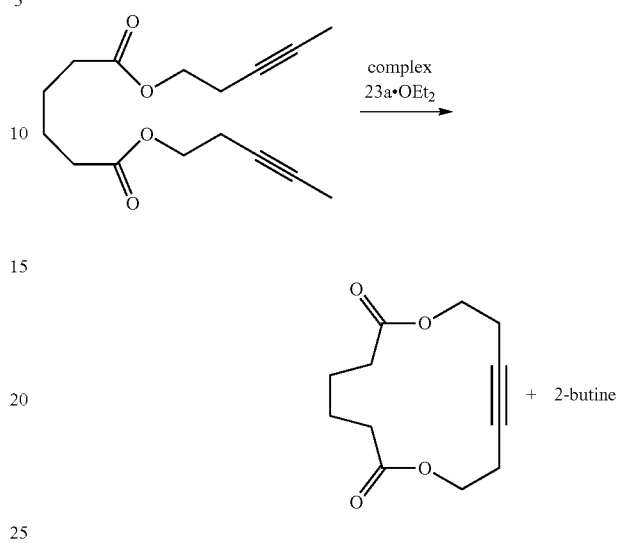

In a dry 100 mL Schlenk-tube, which has been flooded with argon, adipic acid dipent-3-inyl ester (135 mg, 485 μmol), complex 23a.OEt₂ (10.5 mg, 9.67 μmol, 2 mol %) and molecular sieve (970 mg, 5 Å, powder) were suspended in 24.2 mL of toluene. The reaction solution was stirred for 24 h at room temperature, was filtered for the processing over a short silica gel column, the filtrate was concentrated and the residue was purified by means of column chromatography (SiO₂, hexane/EtOAc, 20:1). One obtains 1,8-dioxacyclotetradec-11-in-2,7-dione (100 mg, 92%) as colorless solid. M.p.=109-110° C.; ¹H NMR (400 MHz, CD₂Cl₂): δ=4.13-4.06 (m, 4H), 2.53-2.47 (m, 4H), 2.39-2.30 (m, 4H), 1.76-1.67 (m, 4H); ¹³C NMR (100 MHz, CD₂Cl₂): δ=173.2 (2×C), 78.2 (2×C), 62.8 (2×CH₂), 35.2 (2×CH₂), 25.4 (2×CH₂), 19.4 (2×CH₂); IR (film): ν=2995, 2954, 2937, 2918, 2901, 2872, 1721, 1458, 1425, 1384, 1341, 1272, 1236, 1167, 1140, 1080, 1065, 1021, 981, 931, 843, 124, 699 cm⁻¹; MS (EI) m/z (%): 129 (3), 111 (8), 78 (100), 66 (20), 55 (15), 41 (8); HRMS (ESI): m/z: calculated for C₁₂H₁₆O₄+Na: 247.0941; found: 247.0938.

The following compounds were prepared in an analogous manner. For the obtained yields depending on the selected method, see Table 2.

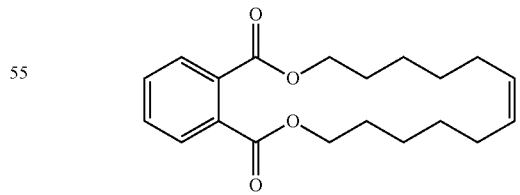

Colorless oil. ¹H NMR (400 MHz, CD₂Cl₂): δ=7.72 (dd, J=5.7, 3.3 Hz, 2H), 7.55 (dd, J=5.7, 3.3 Hz, 2H), 4.32 (t, J=6.0 Hz, 4H), 2.21-2.14 (m, 4H), 1.82-1.73 (m, 4H), 1.60-1.47 (m, 8H); ¹³C NMR (100 MHz, CD₂Cl₂): δ=168.0 (2×C), 132.8 (2×C), 131.3 (2×CH), 129.1 (2×CH), 80.9 (2×C), 66.7 (2×CH₂), 28.7 (2×CH₂), 28.5 (2×CH₂), 26.3 (2×CH₂), 18.9

(2×CH$_2$); IR (film): ν=2928, 2859, 1720, 1600, 1579, 1488, 1460, 1447, 1433, 1385, 1269, 1122, 1070, 1039, 957, 734, 703 cm$^{-1}$; MS (EI) m/z (%): 328 [M$^+$] (8), 180 (9), 162 (30), 149 (100), 133 (17), 122 (18), 121 (26), 119 (14), 108 (43), 107 (18), 105 (15), 95 (11), 94 (24), 93 (44), 91 (29), 81 (19), 80 (28), 79 (34), 77 (13), 67 (19), 55 (13); HRMS (ESI): m/z: calculated for C$_{20}$H$_{24}$O$_4$+Na: 351.1567; found: 351.1567; elemental analysis (%) calculated for C$_{20}$H$_{24}$O$_4$: C, 73.15; H, 7.37; found: C, 73.26; H, 7.28.

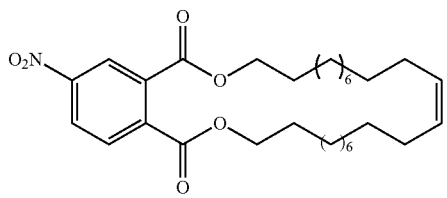

White solid; M.p.=81-82° C.; $^1$H NMR (400 MHz, CDCl$_3$): δ=8.60 (d, J=2.2 Hz, 1H), 8.37 (dd, J=8.4, 2.2 Hz, 1H), 7.85 (d, J=8.4 Hz, 1H), 4.35-4.30 (m, 4H), 2.15 (br s, 4H), 1.74 (sext, J=7.1 Hz, 4H), 1.45-1.29 (m, 28H); $^{13}$C NMR (100 MHz, CDCl$_3$): δ=166.3 (C), 165.2 (C), 148.8 (C), 138.2 (C), 133.2 (C), 130.1 (CH), 125.8 (CH), 124.4 (CH), 80.6 (2×C), 66.7 (2×CH$_2$), 29.6 (2×CH$_2$), 29.5 (CH$_2$), 29.4 (CH$_2$), 29.3 (2×CH$_2$), 29.1 (CH$_2$), 29.1 (CH$_2$), 28.6 (CH$_2$), 28.6 (CH$_2$), 28.5 (CH$_2$), 28.4 (CH$_2$), 28.4 (CH$_2$), 28.4 (CH$_2$), 25.8 (CH$_2$), 25.7 (CH$_2$), 18.5 (2×CH$_2$); IR (film): ν=3108, 3077, 3046, 2918, 2851, 1741, 1720, 1613, 1548, 1532, 1468, 1354, 1298, 1272, 1241, 1136, 1061, 997, 962, 932, 861, 835, 733, 725 cm$^{-1}$; MS (EI) m/z (%): 496 (19), 195 (37), 194 (32), 192 (33), 191 (11), 180 (13), 179 (19), 178 (69), 177 (15), 164 (22), 149 (22), 148 (11), 136 (12), 135 (30), 123 (12), 122 (14), 121 (43), 111 (23), 110 (16), 109 (29), 108 (14), 107 (29), 105 (11), 97 (15), 96 (28), 95 (64), 94 (26), 93 (46), 91 (19), 83 (38), 82 (30), 81 (84), 80 (42), 79 (54), 69 (92), 68 (25), 67 (84), 57 (20), 56 (11), 55 (100), 54 (24), 43 (30), 41 (61); HRMS (ESI): m/z: calculated for C$_{30}$H$_{43}$NO$_6$+Na: 536.2982; found: 536.2989.

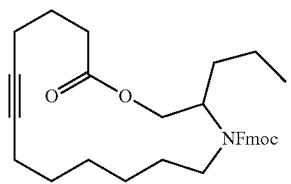

Colorless oil. $^1$H NMR (rotameres, 400 MHz, CDCl$_3$): δ=7.76 (d, J=7.4 Hz, 2H), 7.61-7.53 (m, 2H), 7.42-7.28 (m, 4H), 4.72-4.49 (m, 2H), 4.34-4.24 (m, 2H), 3.88-3.79 (m, 1.5H), 3.41 (br s, 0.5H), 3.02-2.91 (m, 1H), 2.65-2.40 (m, 2H), 2.28-2.15 (m, 3H), 2.13-2.01 (m, 1H), 1.83-1.70 (m, 2H), 1.64-0.77 (m, 14.5H), 0.70 (br s, 1.5H); $^{13}$C NMR (rotameres, 150 MHz, CDCl$_3$): δ=173.3 (C), 173.2 (C), 156.8 (C), 156.4 (C), 144.1 (C), 144.0 (C), 143.9 (C), 141.4 (c), 141.3 (C), 127.6 (CH), 127.5 (CH), 127.1 (CH), 127.0 (CH), 124.6 (CH), 119.9 (CH), 119.8 (CH), 82.7 (C), 79.6 (C), 79.4 (C), 66.5 (CH$_2$), 66.2 (CH$_2$), 63.4 (CH$_2$), 47.5 (CH), 47.3 (CH), 34.9 (CH$_2$), 34.6 (CH$_2$), 34.5 (CH$_2$), 32.4 (CH$_2$), 32.3 (CH$_2$), 28.4 (CH$_2$), 28.2 (CH$_2$), 26.7 (CH$_2$), 26.6 (CH$_2$), 23.5 (CH$_2$), 23.4 (CH$_2$), 19.5 (CH$_2$), 18.2 (CH$_2$), 17.7 (CH$_2$), 14.0 (CH$_3$), 13.8 (CH$_3$); IR film): ν=3065, 3043, 3020, 2931, 2859, 1734, 1688, 1450, 1410, 1386, 1328, 1312, 1292, 1268, 1241, 1222, 1155, 1135, 1054, 1010, 758, 737 cm$^{-1}$; MS (EI) m/z (%): 236 (3), 180 (4), 179 (36), 178 (100), 165 (2); HRMS (ESI): m/z: calculated for C$_{32}$H$_{39}$NO$_4$+Na: 524.2771; found: 524.2776.

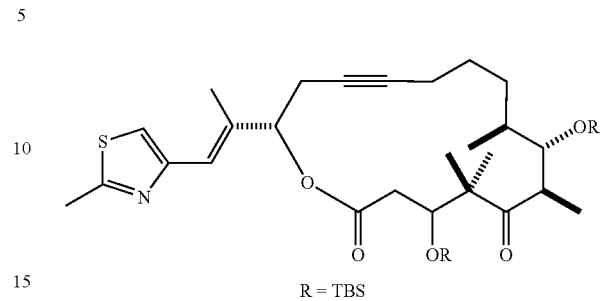

Amorphous solid. [α]$_D^{20}$=−18.5 (c=0.6 in CHCl$_3$); $^1$H NMR (600 MHz, CDCl$_3$): δ=6.96 (s, 1H), 6.55 (br s, 1H), 5.33 (dd, J=7.3, 3.1 Hz, 1H), 4.70 (dd, J=6.4, 5.0 Hz, 1H), 3.93 (dd, J=6.8, 1.9 Hz, 1H), 3.24 (quin., J=6.9 Hz, 1H), 2.78 (dq, J=17.2, 2.8 Hz, 1H), 2.71 (s, 3H), 2.69-2.63 (m, 2H), 2.57 (dd, J=15.3, 5.0 Hz, 1H), 2.27-2.21 (m, 1H), 2.18 (d, J=1.2 Hz, 3H), 2.13-2.07 (m, 1H), 1.78-1.71 (m, 1H), 1.59-1.53 (m, 1H), 1.30-1.20 (m, 2H), 1.41-1.34 (m, 1H), 1.16 (d, J=7.0 Hz, 3H), 1.14 (s, 3H), 1.10 (s, 3H), 0.93 (d, J=6.9 Hz, 3H), 0.91 (s, 9H), 0.86 (s, 9H), 0.1 (s, 3H), 0.09 (s, 3H), 0.08 (s, 3H), 0.07 (s, 3H); $^{13}$C NMR (150 MHz, CDCl$_3$): δ=216.7 (C), 170.1 (C), 164.9 (C), 152.3 (C), 136.9 (C), 120.4 (CH), 116.8 (CH), 82.2 (C), 78.0 (CH), 76.7 (CH), 76.3 (C), 72.6 (CH), 54.5 (C), 44.4 (CH), 41.6 (CH$_2$), 38.9 (CH), 29.5 (CH$_2$), 26.2 (3×CH$_3$), 26.1 (3×CH$_3$), 25.9 (CH$_2$), 24.1 (CH$_2$), 20.9 (CH$_3$), 20.5 (CH$_3$), 19.3 (C), 18.6 (CH$_3$), 18.5 (CH$_2$), 18.3 (C), 17.0 (2×CH$_3$), 15.0 (CH$_3$), −3.2 (CH$_3$), −3.7 (CH$_3$), −4.0 (CH$_3$), −4.1 (CH$_3$); IR (film): ν=2952, 2929, 2894, 2856, 1739, 1702, 1505, 1472, 1463, 1385, 1361, 1254, 1182, 1152, 1097, 1085, 1039, 1018, 1007, 988, 836, 775 cm$^{-1}$; MS (EI) m/z (%): 703 [M$^+$] (5), 648 (23), 647 (47), 646 (97), 604 (11), 446 (14), 445 (33), 444 (100), 402 (22), 344 (15), 270 (38), 195 (12), 185 (18), 178 (12), 151 (21), 143 (13), 115 (13), 101 (12), 75 (45), 73 (51); HRMS (ESI): m/z: calculated for C$_{38}$H$_{65}$NO$_5$SSi$_2$+Na: 726.4014; found: 726.4015.

11. Alkyne Metathesis by Activation of [Mo(≡N)(OSiPh$_3$)$_3$(Phen)] by Means of MnCl$_2$ Prior to the Addition of the Substrate

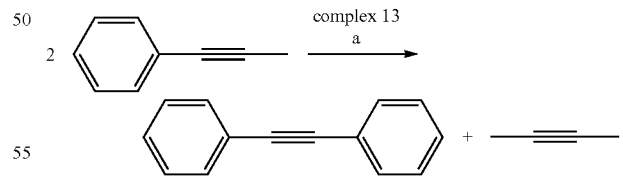

In a dry 25 mL Schlenk-tube, which has been flooded with argon, [Mo(≡N)(OSiPh$_3$)$_3$(phen)].0.5 toluene (0.100 mmol, 116.2 mg), MnCl$_2$ (0.100 mmol, 12.6 mg) and molecular sieve (1.00 g, 5 Å, powder) were suspended in 5 mL of toluene and the mixture was heated to 80° C. After 30 min 1-penyl-1-propine (1.00 mmol, 116.2 mg) were added, the reaction mixture was stirred for 3 h at 80° C. and was filtered after cooling over a short silica gel column. The filtrate was concentrated and the residue was purified by column chromatography (hexane). 88.2 mg of tolane (99%) were isolated as white solid, the spectroscopic and analytical data of which were identical to those of a commercial sample. M.p.=59-61° C.

12. Alkyne metathesis by activation of [Mo(≡N)(OSiPh₃)₃(phen)] by means of MnCl₂ in the presence of the substrate In a dry 25 mL Schlenk-tube, which has been flooded with argon, 1-phenyl-1-propine (1.00 mmol, 116.2 mg), [Mo(≡N)(OSiPh₃)₃(phen)].0.5 toluene (0.100 mmol, 116.2 mg), MnCl₂ (0.100 mmol, 12.6 mg) and molecular sieve (1.00 g, 5 Å, powder) were suspended in 5 mL of toluene. The reaction solution was stirred for 3 h at 80° C. and was filtered after the cooling over a silica gel column. The filtrate was concentrated and the residue was purified by column chromatography (hexane). 88.1 mg of tolane (98%) were isolated as a white solid, the spectroscopic and analytical data of which were identical to those of a commercial sample. M.p.=59-61° C.

13. Alkyne Metathesis without Addition of Molecular Sieve by Activation of [Mo(≡N)(OSiPh₃)₃(Phen)] by Means of MnCl₂ in the Presence of the Substrate In a dry 10 mL Schlenk-tube, which has been flooded with argon, [Mo(≡N)(OSiPh₃)₃(phen)].0.5 toluene (50.0 μmol, 58.1 mg) and MnCl₂ (50.0 μmol, 6.3 mg) were suspended in 2.5 mL of toluene. After addition of 1-phenyl-1-propine (500 μmol, 58.1 mg), the reaction solution was stirred for 24 h at 80° C. and was filtered after cooling over a short silica gel column. The filtrate was concentrated and the residue was purified by column chromatography (hexane). 41.6 mg of tolane (93%) were isolated as white solid, the spectroscopic and analytical data of which were identical to those of a commercial sample. M.p.=59-61° C.

14. Alkyne Metathesis without Addition of Molecular Sieve by Activation of [Mo(≡N)(OSiPh₃)₃(phen)] by Means of CuCl₂ in the Presence of the Substrate In a dry 10 mL Schlenk-tube, which has been flooded with argon, [Mo(≡N)(OSiPh₃)₃(phen)].0.5 toluene (58.8.0 μmol, 68.3 mg) and dried CuCl₂ (58.8 μmol, 7.9 mg) were suspended in 2.5 mL of toluene. After addition of 1-phenyl-1-propine (588 μmol, 68.3 mg), the reaction solution was stirred for 24 h at 80° C. and was filtered after cooling over a short silica gel column (2 cm). The filtrate was concentrated and the residue was purified by column chromatography (hexane). 41.0 mg of tolane (78%) were isolated as a white solid, the spectroscopic and analytical data of which were identical to those of a commercial sample. M.p.=59-61° C.

15. Alkyne Metathesis Using Complex 23a.Et₂O

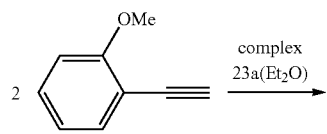

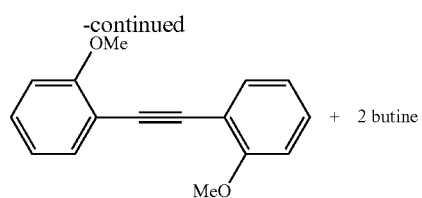

In a dry 25 mL Schlenk-tube, which has been flooded with argon, 1-methoxy-2-(prop-1-yl)benzene (146 mg, 1 mmol), complex 23a.(Et₂O) (22 mg, 0.02 mmol, 2 mol %) and molecular sieve (1 g, 5 Å, powder) were suspended in 5 mL of toluene. The reaction mixture was stirred for 2 h at room temperature, was filtered over a short silica gel column (2 cm), the filtrate was concentrated and the residue was purified by column chromatography (SiO₂, hexane/EtOAc, 20:1). 1,2-bis(2-methoxyphenyl)ethine (115 mg, 0.48 mmol, 97%) was obtained as colorless solid. M.p.=126-127° C.; ¹HNMR (400 MHz, CD₂Cl₂): δ=7.49 (ddd, J=7.3, 1.6, 0.5 Hz, 2H), 7.33 (ddd, J=7.9, 7.7, 1.9 Hz, 2H), 6.95 (td, J=7.9, 1.0 Hz, 4H), 3.92 (s, 6H); ¹³C NMR (100 MHz, CD₂Cl₂): δ=160.3 (2×C), 133.7 (2×CH), 130.1 (2×CH), 120.8 (2×CH), 113.0 (2×C), 111.3 (2×CH), 90.1 (2×C), 56.2 (2×CH₃); IR (film): v=3105, 3033, 2998, 2963, 2937, 2833, 1945, 1903, 1863, 1598, 1574, 1498, 1464, 1456, 1432, 1274, 1241, 1184, 1162, 1115, 1047, 1020, 937, 750 cm⁻¹; MS (EI) m/z (%): 238 [M⁺] (100), 237 (32), 223 (23), 221 (15), 207 (10), 195 (5), 178 (8), 165 (14), 152 (9), 131 (19), 111 (6), 97 (3), 89 (3); HRMS (ESI): m/z: calculated for O₁₆H₁₄O₂+Na: 261.0886; found: 261.0884.

16. Alkyne Metathesis by Activation of [Mo(≡CPh)(OSiPh₃)₃(phen)] (24a) by Means of MnCl₂ Prior to the Addition of the Substrate

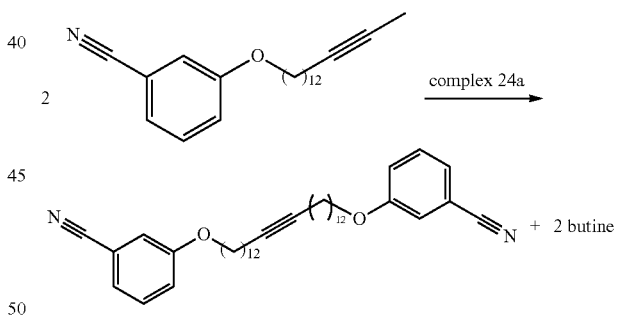

In a dry 25 mL Schlenk-tube, which has been flooded with argon, complex 24a (60 mg, 0.05 mmol, 5 mol %) MnCl₂ (6.3 mg, 0.05 mmol) were dissolved 1 mL of toluene. Subsequently, the mixture was heated for 30 min to 100° C. and was then re-cooled to room temperature. The catalyst solution was transferred into a suspension of 3-cyanobenzoic acid pentadec-13-inyl ester (325 mg, 1 mmol) and molecular sieve (1 g, 5 Å, powder) in 4 mL of toluene, and the reaction mixture was stirred for 2 h at room temperature. Finally, it was filtered over a short silica gel column (2 cm), the filtrate was concentrated and the residue was purified by column chromatography (SiO₂, hexane/EtOAc, 20:1). One obtains the product (265 mg, 89%) as colorless solid. ¹H NMR (400 MHz, CDCl₃): δ(ppm)=7.35 (td, J=7.6, 1.2 Hz, 2H), 7.22 (dt, J=7.6, 1.2 Hz, 2H), 7.12-7.10 (m, 4H), 3.95 (t, J=6.5 Hz, 4H), 2.13 (t, J=7.1 Hz, 4H), 1.78 (quint., J=8.0 Hz, 4H), 1.50-1.41 (m, 8H), 1.36-1.28 (m, 28H). $^{13}$C NMR (100 MHz, CDCl$_3$): δ(ppm) =159.2, 134.9, 130.2, 130.1, 127.9, 124.2, 119.8, 118.8, 117.3, 113.1, 80.2, 68.4, 29.6, 29.5, 29.3, 29.1, 29.0, 28.8, 25.9, 18.7. IR (film): v=3087, 2918, 2851, 2230, 1957, 1739, 1606, 1576, 1523, 1473, 1444, 1428, 1405, 1319, 1291, 1256, 1185, 1163, 1144, 1118, 1048, 1026, 999, 988, 904, 870, 834, 799, 782, 761, 738, 718, 698, 681 cm$^{-1}$. MS (EI) m/z (%): 596 [M$^+$] (100), 553 (6), 478 (7), 394 (6), 380 (11), 366 (17), 352 (15), 339 (47), 325 (73), 310 (15), 296 (13), 283 (8), 151 (6), 137 (11), 132 (9), 123 (18), 109 (34), 95 (66), 81 (67), 67 (49), 55 (68), 41 (21).

The following compounds have been prepared in an analogous manner; see Table 1 with respect to the yields in dependence of the used method:

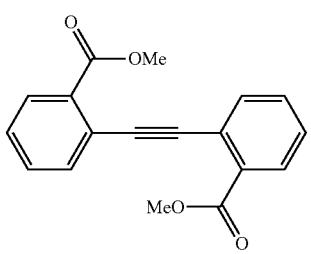 [SMILES: COC(=O)c1ccccc1C#Cc1ccccc1C(=O)OC]

Dimethyl 2,2'-(ethine-1,2-diyl)dibenzoate. Yellow solid, m.p.=83-84° C.; $^1$H NMR (400 MHz, CDCl$_3$): δ=7.97-8.00 (m, 2H), 7.73 (ddd, J=7.3, 1.2, 0.4 Hz, 2H), 7.51 (dt, J=7.6, 1.4 Hz, 2H), 7.39 (dt, J=7.7, 1.3 Hz, 2H), 3.96 (s, 6H); $^{13}$C NMR (100 MHz, CDCl$_3$): δ=166.6, 134.3, 131.8, 131.7, 130.4, 128.1, 123.8, 93.1, 52.2; IR (ATR) v=2950, 1725, 1714, 1595, 1567, 1491, 1448, 1431, 1292, 1250, 1189, 1128, 1077, 1041, 963, 755, 699 cm$^{-1}$; MS (EI) m/z (%): 294 (11) [M$^+$], 280 (18), 279 (100), 265 (5), 264 (24), 248 (20), 220 (16), 176 (5), 163 (8), 132 (10), 102 (7), 88 (9); HRMS (ESI): m/z: calculated for O$_{18}$H$_{14}$O$_4$+Na: 317.0784. found: 317.0785.

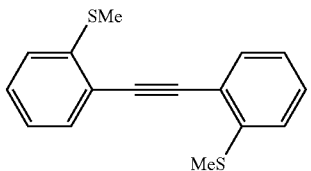 [SMILES: CSc1ccccc1C#Cc1ccccc1SC]

1,2-bis(2-(methylthio)phenyl)ethine. Colorless solid. M.p.=123-124° C.; $^1$H NMR (400 MHz, CD$_2$Cl$_2$): δ=7.52 (ddd, J=7.9, 1.5, 0.5 Hz, 2H), 7.34 (ddd, J=8.1, 7.4, 1.5 Hz, 2H), 7.22 (dd, J=8.1, 0.7 Hz, 2H), 7.14 (td, J=7.4, 1.2 Hz, 2H), 2.52 (s, 6H); $^{13}$C NMR (100 MHz, CD$_2$Cl$_2$): δ=142.2 (2×0), 132.8 (2×CH), 129.4 (2×CH), 124.6 (2×CH), 124.5 (2×CH), 121.4 (2×C), 93.4 (2×C), 15.3 (2×CH$_3$); IR (film): v=3086, 3053, 3011, 2915, 2854, 2830, 1954, 1909, 1868, 1827, 1781, 1584, 1555, 1470, 1432, 1279, 1245, 1125, 1074, 1036, 972, 954 cm$^{-1}$; MS (EI) m/z (%): 270 [M$^+$] (16), 255 (53), 241 (17), 240 (100), 221 (19), 208 (6), 195 (5), 163 (5), 120 (15); HRMS (ES): m/z: calculated for C$_{16}$H$_{14}$S$_2$: 270.0537; found: 270.0535.

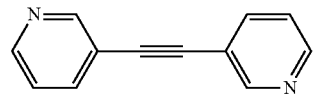

1,2-di(pyridine-3-yl)ethine. Light-yellow solid. $^1$H NMR (400 MHz, CDCl$_3$): δ=8.79 (br s, 2H); 8.58 (d, J=4.0 Hz, 2H), 7.83 (dt, J=7.8, 1.8 Hz, 2H), 7.31 (dd, J=7.8, 5.0 Hz, 2H); $^{13}$C NMR (100 MHz, CDCl$_3$): δ=152.4, 149.2, 138.7, 123.3, 119.9, 89.3; IR (film): 3029, 2924, 1987, 1952, 1916, 1881, 1771, 1727, 1558, 1480, 1410, 1328, 1295, 1254, 1187, 1127, 1097, 1040, 1018, 959, 926, 882, 850, 809, 701 cm$^{-1}$; MS (EI) m/z (%): 180 (100) [M$^+$], 153 (7), 152 (6), 127 (11), 128 (5), 100 (6), 99 (5), 76 (5), 74 (12), 63 (5); HRMS (EI): m/z: calculated for C$_{12}$H$_8$N$_2$ [M$^+$]: 180.0687; found: 180.0686.

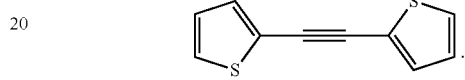

1,2-di(thiophene-2-yl)ethine. Colorless solid. M.p.=98-99° C.; $^1$H NMR (400 MHz, CD$_2$Cl$_2$): δ=7.35 (dd, J=5.2, 1.1 Hz, 2H), 7.29 (dd, J=3.6, 1.1 Hz, 2H), 7.04 (dd, J=5.2, 3.6 Hz, 2H); $^{13}$C NMR (100 MHz, CD$_2$Cl$_2$): δ=132.5 (2×CH), 128.2 (2×CH), 127.6 (2×CH), 123.1 (2×C), 86.4 (2×CH); IR (film): v=3100, 3082, 1791, 1723, 1651, 1596, 1432, 1406, 1195, 1098, 1040, 1028, 849, 824, 692 cm$^{-1}$; MS (EI) m/z (%): 192 (9), 191 (13), 190 (100), 158 (8), 145 (13), 114 (9), 95 (8), 69 (6), 45 (5); HRMS (EI): m/z: calculated for O$_{10}$H$_6$S$_2$: 189.9911; found: 189.9912.

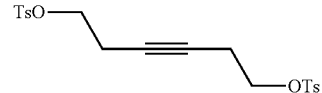

Hex-3-ine-1,6-diyl bis(4-methylbenzene sulfonate). Colorless solid. M. p.=83-84° C.; $^1$H NMR (400 MHz, CDCl$_3$): δ=7.77-7.80 (m, 4H), 7.34-7.36 (m, 4H), 4.01 (t, J=7.0 Hz, 4H), 2.44-2.47 (m, 10H); $^{13}$C NMR (100 MHz, CDCl$_3$): δ=145.0, 132.9, 129.9, 127.9, 76.8, 67.7, 21.6, 19.6; IR (film): v=2955, 2920, 1597, 1453, 1352, 1293, 1190, 1170, 1096, 969, 898, 841, 813, 761, 662 cm$^{-1}$; MS (EI) m/z (%): 423 (5), 422 (21) [M$^+$], 251 (11), 250 (10), 186 (6), 156 (8), 155 (86), 139 (21), 92 (9), 91 (100), 90 (7), 79 (10), 78 (62), 77 (9), 66 (7), 65 (47); HRMS (ESI): m/z: calculated for [C$_{20}$H$_{22}$O$_6$S$_2$+Na]: 445.0750; found: 445.0750.

17. Alkyne Cross-Metathesis Using [Mo(≡CPh)(OSiPh$_3$)$_3$(Et$_2$O)] (23a.Et$_2$O)

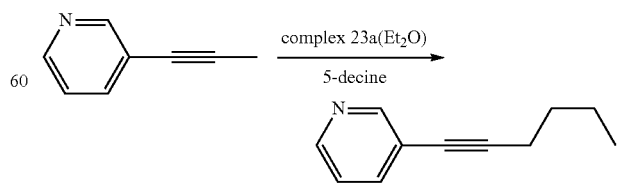

In a dry 25 mL Schlenk-tube, which has been flooded with argon, 3-(prop-1-yl)-pyridine (117 mg, 1.00 mmol), 5-decine (346 mg, 2.50 mmol), complex 23a.Et$_2$O (10.5 mg, 9.67 μmol, 2 mol %) and molecular sieve (1 g, 5 Å, powder), were suspended in 5 mL of toluene. The reaction mixture was stirred for 4 h at room temperature and was filtered for processing through a short silica gel column. The filtrate was concentrated and the residue was purified by column chromatography (SiO$_2$, hexane/EtOAc, 20:1). One obtains the metathesis product (103 mg, 65%) as colorless oil. $^1$H NMR (400 MHz, CDCl$_3$): δ(ppm)=8.61 (d, J=1.5 Hz, 1H), 8.46 (dd, J=4.9, 1.6 Hz, 1H), 7.66 (dt, J=7.9, 1.9 Hz, 1H), 7.19 (ddd, J=7.9, 4.9, 0.8 Hz, 1H), 2.42 (t, J=7.0 Hz, 2H), 1.63-1.56 (m, 2H), 1.52-1.43 (m, 2H), 0.95 (t, J=7.2 Hz, 3H). $^{13}$C NMR (100 MHz, CDCl$_3$): δ(ppm)=152.3, 147.8, 138.4, 127.8, 122.8, 121.2, 94.0, 30.6, 22.0, 19.1, 13.6. IR (film): ν=3030, 2957, 2932, 2872, 2229, 1584, 1558, 1475, 1429, 1406, 1379, 1363, 1328, 1301, 1263, 1185, 1118, 1101, 1023, 1007, 949, 923, 889, 802, 747, 704 cm$^{-1}$. MS (EI) m/z (%): 159 [M$^+$] (52), 144 (100), 130 (46), 116 (45), 103 (25), 89 (32), 77 (13), 63 (39), 51 (14), 41 (15), 39 (15), 27 (17).

18. Cyclooligomerization Via Alkyne Metathesis Using [Mo(≡CPh)(OSiPh$_3$)$_3$(Et$_2$O)] (23a.Et$_2$O)]

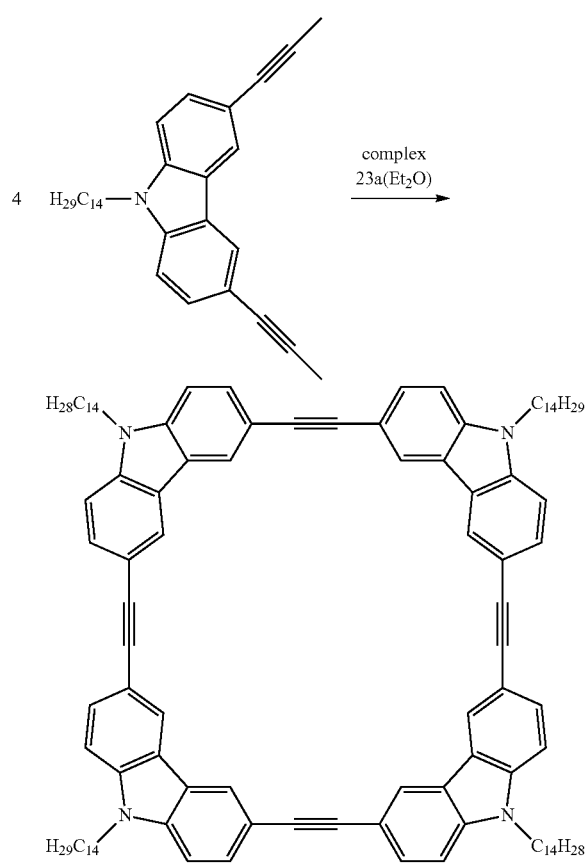

In a dry 25 mL Schlenk-tube, which has been flooded with argon, 3,6-di(prop-1-inyl)-9-tetradecyl-9H-carbazole (439 mg, 1.00 mmol), complex 23a.Et$_2$O (22 mg, 0.02 mmol, 2 mol %) and molecular sieve (1 g, 5 Å, powder) were suspended in 5 mL of toluene. The reaction solution was stirred for 4 h at room temperature and was filtered for processing over a short silica gel column. After concentration of the filtrate and purification by means of column chromatography of the residue (SiO$_2$, hexane/CHCl$_3$, 1:1) it is recrystallized from CH$_2$Cl$_2$/methanol (1:1) and the tetramer is obtained as colorless solid (316 mg, 82%). $^1$H NMR (400 MHz, CD$_2$Cl$_2$): δ(ppm)=8.43 (s, 2H), 7.72 (dd, J=8.3, 1.1 Hz, 2H), 7.40 (d, J=8.4 Hz, 2H), 4.32 (t, J=6.8 Hz, 2H), 1.91 (quin, J=6.8 Hz, 2H), 1.44-1.25 (m, 22H), 0.88 (t, J=6.5 Hz, 2H). $^{13}$C NMR (100 MHz, CD$_2$Cl$_2$): δ(ppm)=140.2, 129.3, 124.0, 122.7, 114.5, 108.9, 89.0. 31.9, 29.7, 29.67, 29.64, 29.60, 29.55, 29.50, 29.4, 29.0, 27.3, 22.7, 14.1.

II. Preparation and Use of Further Preferred Catalysts and the Bipyridine Adducts Thereof The bipyridine derivatives, which were used for the preparation of the complexes, were dissolved in toluene and the solution was dried over molecular sieve 5 Å (MS 5 Å). Subsequently, the toluene was distilled off in vacuo and the remaining bipyridine derivative was stored under argon.

1. Preparation of [Mo(≡N)(OSiPh$_3$)$_3$(biphy)] (13b)

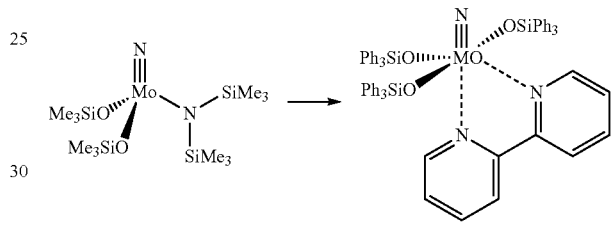

In a dry 50 mL Schlenk-tube, which has been flooded with argon, [Mo(≡N)(OTMS)$_2$(N(TMS)$_2$)] (1.15 g, 2.57 mmol) was provided and was dissolved in 25 mL of dry toluene. Ph$_3$SiOH (7.13 g, 7.71 mmol) was added in argon counterflow and the obtained yellowish solution was stirred for 30 min at room temperature. The solution was transferred to a 100 mL Schlenk-tube, which already contained 2,2'-bipyridine (0.401 g, 2.57 mmol). The obtained reaction mixture turned to a clear yellowish solution after few minutes, some minutes later a light-yellow precipitation was slowly formed. The solvent was removed after 30 min and the obtained residue was dried for 1 h at room temperature in high vacuum (10$^{-3}$ mbar) and for 1 h at 60° C. in high vacuum (10$^{-3}$ mbar). The thus obtained yellow solid was recrystallized twice from hot toluene. For this, at first it was dissolved in about 50 mL of hot toluene (105° C.), wherein a remaining insoluble residue was removed by filtration of the hot solution. Then, the solution was slowly cooled down to room temperature and was left for two days. Subsequently, the green solution was decanted from the yellow crystals (0.743 g) and the crystals were dried in vacuo. The mother liquor was concentrated at room temperature up to dryness and the before-described procedure was repeated with about 25 mL of hot toluene. Further 1.355 g product were obtained. In total, 2.098 g [Mo(≡N)(OSiPh$_3$(bipy)] were obtained in the form of yellow crystals. Depending on the dryness degree, the solid may contain varying amounts of toluene. This complex can be stored at air over months without recognizable decomposition. $^1$H NMR (400 MHz, CD$_2$Cl$_2$): δ=8.93 (dd, J=5.5, 1.1 Hz, 1H), 8.72-8.71 (m, 1H), 7.81 (dd, J=8.0, 1.6 Hz, 6H), 7.77 (td, J=7.9, 1.6 Hz, 1H), 7.48 (d, J=8.2 Hz, 1H), 7.39 (td, J=7.9, 1.6 Hz, 1H), 7.27-7.16 (m, 23H), 7.07 (t, J=7.8 Hz, 6H), 6.97 (t, J=7.8 Hz, 12H), 6.73-6.70 (m, 1H). $^{13}$C NMR (100 MHz, CD$_2$Cl$_2$): δ=156.5, 150.1, 149.9, 147.8, 139.5, 138.3, 138.0, 137.9, 136.1, 135.5, 135.3, 135.2, 129.6, 129.5, 129.8, 127.9, 127.8, 127.6, 125.6, 125.4, 122.1, 122.0.

Figure 8:
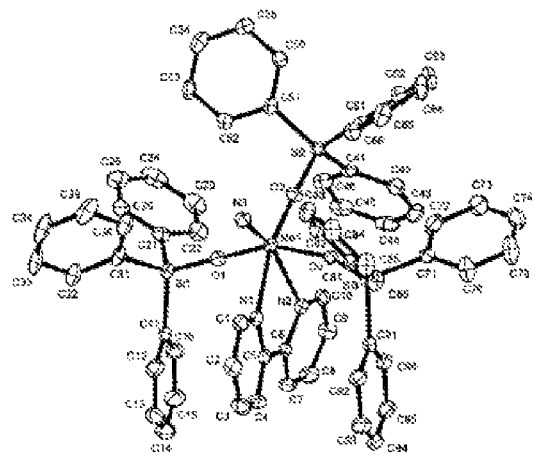

The Crystal Structure of Mo(≡N)(OSiPh₃(bipy) is Presented in FIG. 8.

2. Preparation of [Mo(≡N)(OSiPh₃(4,4'-di-tert-butyl-2,2'-dipyridyl)] (13e)

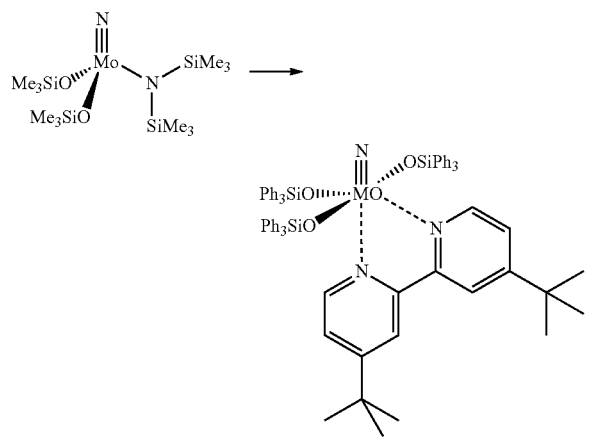

Figure 9:
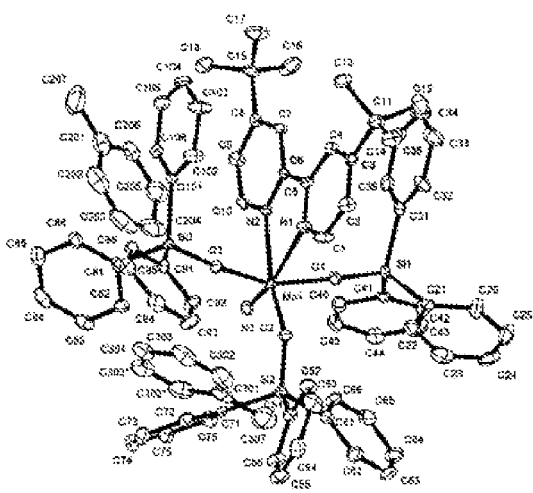

In a dry 10 mL Schlenk-tube, which has been flooded with argon, [Mo(≡N)(OTMS)₂(N(TMS)₂)] (67.3 mg, 0.15 mmol), was provided and was dissolved in 1.5 mL of dry toluene. Ph₃SiOH (124.4 mg, 0.45 mmol) was added in argon counter-flow and the obtained yellowish solution was stirred for 30 min at room temperature. The solution was transferred to a 10 mL Schlenk-tube, which already contained 4,4'-di-tert-butyl-2,2'-dipyridyl (40.3 mg, 0.15 mmol). After few minutes, the obtained reaction mixture turned to a clear yellowish solution, after about 1 h a light-yellow precipitation was slowly formed. After 1.5 h, the solvent was removed and the obtained residue was dried for 1 h at room temperature in high vacuum ($10^{-3}$ mbar) and for 1 h at 60° C. in high vacuum ($10^{-3}$ mbar). The thus obtained solid was recrystallized from hot toluene (2 mL). Crystals were obtained, which were suitable for a crystal structure analysis. The structure of the complex is shown in FIG. 9.

3. Preparation of [Mo(≡CPh)(OSiPh₃)₃(biphy)] (24b)

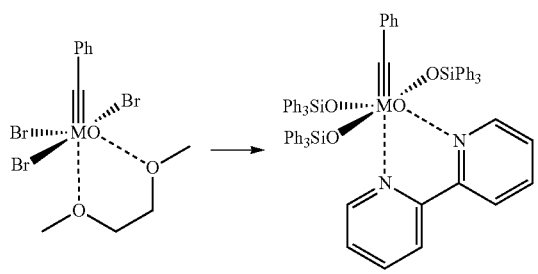

In a dry 100 mL Schlenk-tube, which has been flooded with argon, Mo(≡CPh)Br₃(dme) (855 mg, 1.66 mmol), was dissolved in 25 mL of toluene and was treated with a solution of Ph₃SiOK (2.09 g, 6.64 mmol) in 25 mL of toluene. After 1 h at room temperature, it was filtered and the filtrate was dropped to a solution of 2,2'-bipyridine (259 mg, 1.66 mmol) in 5 mL of toluene, wherein an intensive violet color occurs; the solution appears nearly black with increasing concentration. After 1 h at room temperature, 35 mL of diethyl ether were added to the solution, and the reaction mixture was left overnight for crystallization. The solid was washed twice with 10 mL of diethyl ether, respectively. After drying in high vacuum, Mo(≡CPh)(OSiPh₃)₃(biphy) was obtained as violet solid (1.46 g, 75%). ¹H NMR (600 MHz, CD₂Cl₂): δ=9.04 (dd, J=5.0, 1.0 Hz, 1H), 8.62 (dd, J=5.4, 1.1 Hz, 1H), 7.87 (dd, J=8.0, 1.4 Hz, 5H), 7.82 (td, (J=7.9, 1.7 Hz, 1H), 7.65 (d, J=6.9 Hz, 1H), 7.61 (d, J=8.3 Hz, 1H), 7.51 (dd, J=8.0, 1.4 Hz, 2H), 7.41 (tt, J=8.9, 1.4 Hz, 2H), 7.35 (td, J=7.9, 1.7 Hz, 1H), 7.31-7.28 (m, 4H), 7.23 (dd, J=7.9, 1.4 Hz, 10H), 7.19 (tt, J=7.5, 1.3 Hz, 3H), 7.15 (tt, J=7.4, 1.3 Hz, 5H), 6.96 (t, J=7.5 Hz, 6H), 6.93 (6.91 (t, J=7.9 Hz, 11H), 6.85 (tt, J=7.4, 1.3 Hz, 1H), 6.51 (tt, J=7.4, 1.3 Hz, 1H), 6.33 (dd, J=8.3, 1.3 Hz, 2H). ¹³C NMR (150 MHz, CD₂Cl₂): δ=291.7, 155.7, 151.6, 151.0, 147.6, 143.3, 139.3, 139.0. 138.6, 138.4, 136.1, 135.7, 135.5, 135.4, 135.2, 131.1, 130.4, 130.2, 129.3, 129.1, 128.7, 128.5, 128.2, 128.1, 127.7, 127.4, 127.1, 126.6, 125.4, 125.0, 122.2, 122.1.

Figure 10:
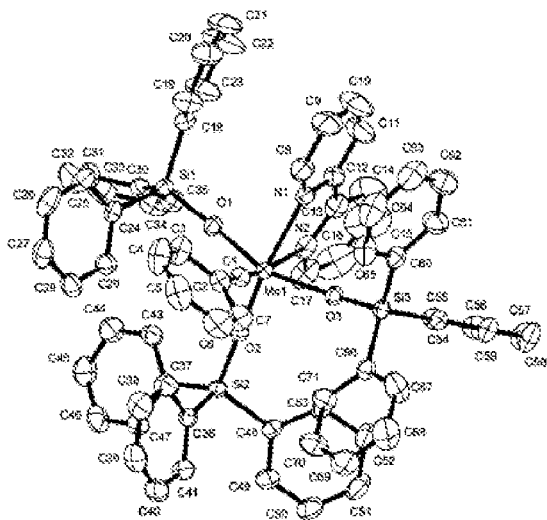

The structure of the complex was confirmed by means of crystal structure analysis (FIG. 10).

4. Preparation of [Mo(≡CPh)(OSiPh₃)₃(4,4'-dimethyl-2,2'-dipyridyl)] (24c)

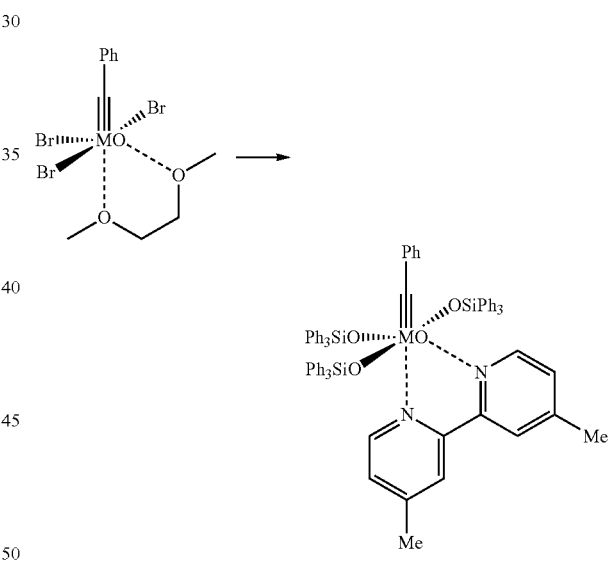

In a dry 100 mL Schlenk-tube, which has been flooded with argon, Mo(≡CPh)Br₃(dme) (46 mg, 89 μmol), was dissolved in 0.55 mL of toluene and was treated with a solution of Ph₃SiOK (112 mg, 357 μmol). After 1 h at room temperature, it was filtered and the filtrate was dropped to a solution of 4,4'-dimethyl-2,2'-dipyridine (16 mg, 89 μmol) in 1 mL of toluene. After 1 h at room temperature, the precipitated violet solid was filtered off and was washed with 5 mL of diethyl ether. After drying in high vacuum, [Mo(≡CPh)(OSiPh₃)₃(4,4'-dimethyl-2,2'-dipyridyl)] was obtained as violet solid (83 mg, 78%). ¹H NMR (600 MHz, CD₂Cl₂): δ=8.85 (d, J=7.9 Hz, 1H), 8.49 (d, J=7.5 Hz, 1H), 8.47 (d, J=8.5 Hz, 1H), 7.86 (dd, J=12.1, 2.1 Hz, 5H), 7.50 (dd, J=12.1, 2.1 Hz, 2H), 7.41-7.36 (m, 2H), 7.32-7.26 (m, 4H), 7.23 (dd, J=12.0, 2.1 Hz, 10H), 7.20-7.09 (m, 8H), 7.04 (m, 1H), 6.96-6.88 (m, 16H), 6.83 ((tt, J=11.1, 2.0 Hz, 2H), 6.34 (dd, J=12.6, 2.0 Hz, 2H), 6.29-6.27 (m, 1H), 2.43 (s, 3H), 2.18 (s, 3H). $^{13}$C NMR (150 MHz, CD$_2$Cl$_2$): δ=291.5, 156.5, 155.3, 151.7, 151.0, 150.5, 150.1, 149.3, 148.5, 147.4, 143.5, 139.5, 139.3, 136.3, 135.9, 135.7, 135.5, 135.4, 135.3, 131.3, 130.3, 129.4, 129.1, 128.7, 128.6, 128.4, 128.2, 127.7, 127.4, 127.2, 126.6, 126.1, 125.7, 125.0, 122.9, 122.2, 66.1, 15.5.

5. Preparation of [Mo(≡CPh)(OSiPh$_3$)$_3$](4,4'-dimethoxy-2,2'-dipyrdidyl)] (24d)

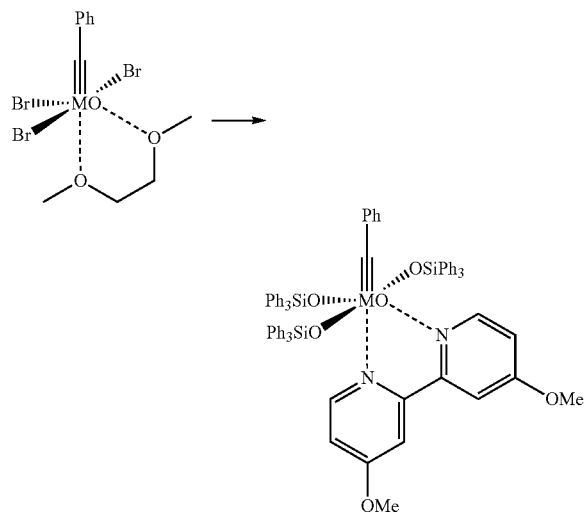

Figure 11:
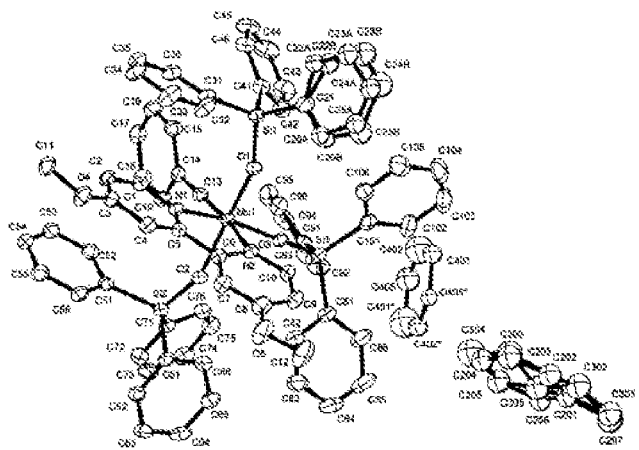

In a dry 100 mL Schlenk-tube, which has been flooded with argon, Mo(≡CPh)Br$_3$(dme) (46 mg, 89 μmol) was dissolved in 0.5 mL of toluene and was treated with a solution of Ph$_3$SiOK (112 mg, 357 μmol) in 0.5 mL of toluene. After 1 h at room temperature, it was filtered and the filtrate was dropped to a solution of 4,4'-dimethoxy-2,2'-bipyridine (19 mg, 89 μmol) in 1 mL of toluene. After 1 h at room temperature, 1 mL of diethyl ether was added to the solution and the mixture was left overnight for crystallization. The precipitate was filtered off and yielded after drying in high vacuum Mo(≡CPh)(OSiPh$_3$)$_3$(4,4'-dimethoxy-2,2'-dipyrdidyl) as a violet crystalline solid (78 mg, 71%). The structure of [Mo(≡CPh)(OSiPh$_3$)$_3$(4,4'-dimethoxy-2,2'-dipyrdidyl)] was confirmed by crystal structure analysis (FIG. 11).

6. Preparation of [Mo(≡CPh)(OSiAr$_3$)$_3$)(bipy)] (Ar=4-methoxyphenyl) (24e)

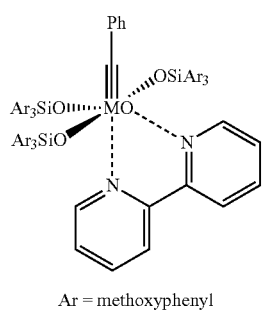

Ar = methoxyphenyl

A solution of [Mo(≡CPh)Br$_3$(dme) (0.21 g, 0.40 mmol) and Ar$_3$SiOK (Ar=4-methoxyphenyl, 0.65 g, 1.6 mmol) in toluene (10 mL) was stirred for 1 h at room temperature under argon. Subsequently, the precipitated solid was filtered off under argon, and the filtrate was treated with a solution of 2,2'-bipyridine (0.13 g, 0.80 mmol) in Et$_2$O (10 mL), and the reaction mixture was stirred for 2 h at room temperature. Subsequently, the solvents were distilled off in vacuo and the residue was treated with Et$_2$O (30 mL). The formed red solution was filtered off from non-dissolved ingredients, the filtrate was concentrated and the residue was recrystallized from CH$_2$Cl$_2$/pentane. One obtains the product as dark-red solid (0.21 g, 36%). $^1$H NMR (400 MHz, CD$_2$Cl$_2$): δ=9.00 (ddd, J=5.0, 1.7, 0.8 Hz, 1H), 8.69 (ddd, J=5.4, 1.6, 0.6 Hz, 1H), 7.86 (ddd, J=7.8, 7.8, 1.8 Hz, 1H), 7.72 (d, J=8.6 Hz, 6H), 7.67 (d, J=8.3 Hz, 1H), 7.44-7.29 (m, 3H), 7.11 (d, J=8.6 Hz, 12H), 6.94 (dd, J=7.4, 7.4 Hz, 2H), 6.84 (tt, J=7.4, 1.3 Hz, 1H), 6.62 (ddd, J=7.2, 5.4, 1.5 Hz, 1H), 6.47 (d, J=8.6 Hz, 6H), 6.45 (d, J=8.6 Hz, 12H), 6.29 (dd, J=7.4, 1.3 Hz, 2H), 3.68 (s, 18H), 3.62 (s, 9H); $^{13}$C NMR (100 MHz, CD$_2$Cl$_2$): δ=291.0, 160.9, 160.6, 156.2, 152.0, 151.5, 148.0, 143.8, 138.5, 138.5, 137.9, 137.3, 131.5, 131.3, 131.0, 127.3, 126.6, 125.4, 125.2, 122.3, 122.3, 113.6, 113.3, 55.4, 55.3.

Figure 12:
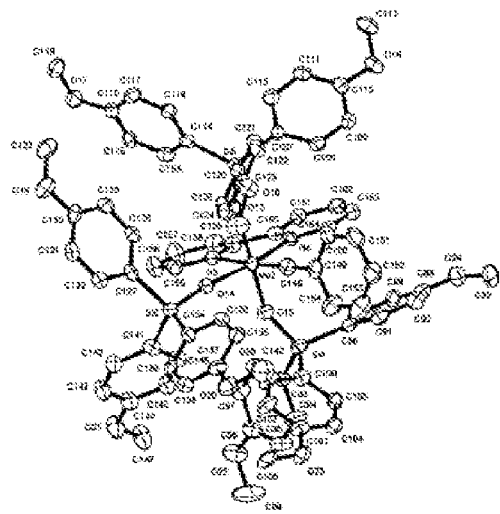

The structure of [Mo(≡CPh)(OSiAr$_3$)$_3$)(bipy)] (Ar=4-methoxyphenyl) was Confirmed by Crystal Structure Analysis (FIG. 12).

7. Alkyne Ring-Closure Metathesis Using [Mo(≡N)(OSiPh$_3$)$_3$)(bipy)]

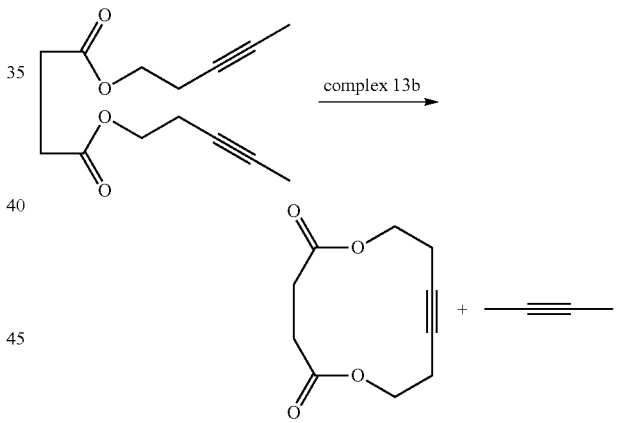

In a dry 100 mL Schlenk-tube, which has been flooded with argon, [Mo(≡N)(OSiPh$_3$)$_3$)(bipy)] (109.2 mg, 0.10 mmol) and MnCl$_2$ (12.6 mg, 0.10 mmol) were suspended in dry toluene (15 mL) and the mixture was heated to 80° C. Additional dry toluene (35 mL) and succinic acid dipent-3-inyl ester (278.3 mg, 1.00 mmol) were added after 30 min, the reaction mixture was stirred for 24 h at 80° C. and was filtered after cooling over a short silica gel column. The filtrate was concentrated and the residue was purified by column chromatography (hexane/EtOAc 4:1). 1,6-dioxacyclododec-9-ine-2,5-dione was isolated as colorless oil (yield: 81%). $^1$H NMR (400 MHz, CD$_2$Cl$_2$): δ=4.21-4.14 (m, 4H), 2.61 (s, 4H), 2.44-2.37 (m, 4H); $^{13}$C NMR (100 MHz, CD$_2$Cl$_2$): δ=171.9 (2×C), 79.0 (2×C), 61.6 (2×CH$_2$), 30.2 (2×CH$_2$), 19.7 (2×CH$_2$); IR (film): ν=2965, 2915, 2840, 1729, 1458, 1421, 1383, 1353, 1336, 1267, 1251, 1158, 1053, 1030, 1000, 952, 837 cm$^{-1}$; MS (EI) m/z (%): 166 (1), 101 (14), 78 (100), 66 (59), 65 (16), 55 (7), 40 (12), 28 (7); HRMS (ESI): m/z: calculated for $C_{10}H_{12}O_4$+Na: 219.0628; found: 219.0627.

8. Alkyne ring-closure metathesis using [Mo(≡CPh)(OSiPh$_3$)$_3$)(bipy)] (24b) and MnCl$_2$

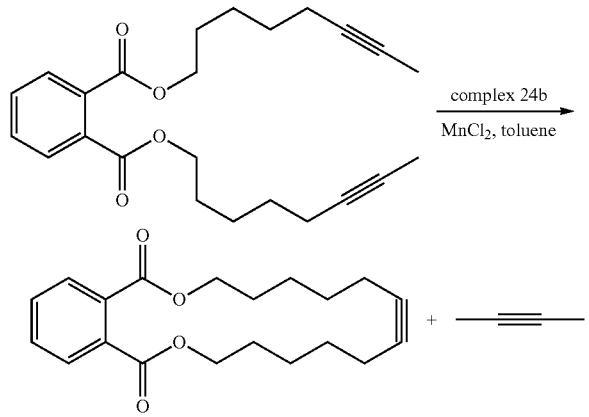

In a dry 25 mL Schlenk-tube, which has been flooded with argon, complex 24b (43 mg, 37 µmol, 5 mol %) and MnCl$_2$ (4.6 mg, 37 µmol) were dissolved in 1 mL of toluene. Subsequently, the mixture was heated for 30 min to 80° C. and was re-cooled to room temperature. The formed solution of the catalyst was added to a suspension of bis(oct-6-inyl)phthalate (282 mg, 737 µmol) and molecular sieve (737 mg, 5 Å, powder) in 36 mL of toluene, and the mixture was stirred for 24 h at room temperature. After cooling, it was filtered over a short silica gel column, the filtrate was concentrated and the residue was purified by means of column chromatography (hexane/EtOAc 9:1). The product was isolated as colorless oil (218 mg, 90%). $^1$H NMR (400 MHz, CD$_2$Cl$_2$): δ=7.72 (dd, J=5.7, 3.3 Hz, 2H), 7.55 (dd, J=5.7, 3.3 Hz, 2H), 4.32 (t, J=6.0 Hz, 4H), 2.21-2.14 (m, 4H), 1.82-1.73 (m, 4H), 1.60-1.47 (m, 8H); $^{13}$C NMR (100 MHz, CD$_2$Cl$_2$): δ=168.0 (2×C), 132.8 (2×C), 131.3 (2×CH), 129.1 (2×CH), 80.9 (2×C), 66.7 (2×CH$_2$), 28.7 (2×CH$_2$), 28.5 (2×CH$_2$), 26.3 (2×CH$_2$), 18.9 (2×CH$_2$); IR (film): v=2928, 2859, 1720, 1600, 1579, 1488, 1460, 1447, 1433, 1385, 1269, 1122, 1070, 1039, 957, 734, 703 cm$^{-1}$; MS (EI) m/z (%): 328 [M$^+$] (8), 180 (9), 162 (30), 149 (100), 133 (17), 122 (18), 121 (26), 119 (14), 108 (43), 107 (18), 105 (15), 95 (11), 94 (24), 93 (44), 91 (29), 81 (19), 80 (28), 79 (34), 77 (13), 67 (19), 55 (13); HRMS (ESI): m/z: calculated for $C_{20}H_{24}O_4$+Na: 351.1567. found: 351.1567; elemental analysis (%) calculated for $C_{20}H_{24}O_4$: C, 73.15; H, 7.37. found: C, 73.26; H, 7.28.

For further examples of compounds that were synthesized in an analogous manner, see Table 2.

9. Alkyne Metathesis by Activation of [Mo(≡N)(OSiPh$_3$)$_3$)(bipy)] (24b) by Means of MnCl$_2$ Prior to the Addition of the Substrate

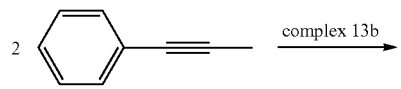

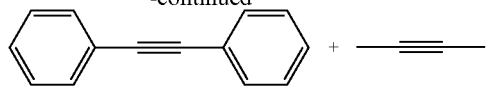

In a dry 25 mL Schlenk-tube, which has been flooded with argon, [Mo(≡N)(OSiPh$_3$)$_3$)(bipy)] (109.2 mg, 0.10 mmol), MnCl$_2$ (12.6 mg, 0.10 mmol) and molecular sieve 5 Å (1.0 g) was suspended in dry toluene (5 mL) and the mixture was heated to 80° C. After 30 min, 1-phenyl-1-propine (116.2 mg, 1.00 mmol) was added, the reaction mixture was stirred for 3 h at 80° C. and was filtered after cooling over a short silica gel column. The filtrate was concentrated and the residue was purified by means of column chromatography (hexane). 88.2 mg of tolane (99%) were isolated as a white solid, the spectroscopic and analytical data were identical to those of a commercial sample. M.p.=59-61° C.

10. Alkyne Metathesis by Activation of [Mo(≡N)(OSiPh$_3$)$_3$)(bipy)] by Means of MnCl$_2$ in Presence of the Substrate In a 25 mL Schlenk-tube, which has been flooded with argon, [Mo(≡N)(OSiPh$_3$)$_3$)(bipy)] (109.2 mg, 0.10 mmol), MnCl$_2$ (12.6 mg, 0.10 mmol), molecular sieve 5 Å (1.0 g) and 1-phenyl-1-propine (116.2 mg, 1.00 mmol) were suspended in dry toluene (5 mL). The reaction mixture was stirred for 3 h at 80° C. and was filtered after cooling over a short silica gel column. The filtrate was concentrated and the residue was purified by means of column chromatography (hexane). 88.0 mg of tolane (98%) were obtained as a white solid, the spectroscopic and analytical data thereof were identical with those of a commercial sample. M.p.=59-61° C.

For further examples of compounds, which were produced in an analogous manner, see Tables 1 and 2.

11. Alkyne Metathesis without Addition of Molecular Sieve by Activation of [Mo(≡N)(OSiPh$_3$)$_3$)(bipy)] by Means of MnCl$_2$ in Presence of the Substrate In a dry 25 mL Schlenk-tube, which has been flooded with argon, [Mo(≡N)(OSiPh$_3$)$_3$)(bipy)] (109.2 mg, 0.10 mmol), MnCl$_2$ (12.6 mg, 0.10 mmol), and 1-phenyl-1-propine (116.2 mg, 1.00 mmol) were suspended in dry toluene (5 mL). The reaction mixture was stirred for 3 h at 80° C. and was filtered after cooling over a short silica gel column. The filtrate was concentrated and the residue was purified by means of column chromatography (hexane). 77.3 mg of tolane (87%) were isolated as white solid, the spectroscopic and analytical data of which were identical with those of a commercial sample. M.p.=59-61° C.

12. Alkyne Metathesis without Addition of Molecular Sieve by Activation of [Mo(≡N)(OSiPh$_3$)$_3$)(bipy)] by Means of CuCl$_2$ in Presence of the Substrate In a dry 25 mL Schlenk-tube, which has been flooded with argon, [Mo(≡N)(OSiPh$_3$)$_3$)(bipy)] (109.2 mg, 0.10 mmol), CuCl$_2$ (13.4 mg, 0.10 mmol), and 1-phenyl-1-propine (116.2 mg, 1.00 mmol) were suspended in dry toluene (5 mL). The reaction mixture was stirred for 3 h at 80° C. and was filtered after cooling over a short silica gel column. The filtrate was concentrated and the residue was purified by means of column chromatography (hexane). 76.1 mg of tolane (85%)

were isolated as white solid, the spectroscopic and analytical data of which were identical to those of a commercial sample. M.p.=59-61° C.

13. Alkyne Metathesis by Activation of [Mo(≡CPh)(OSiPh₃)₃(bipy)] (24b) by Means of MnCl₂

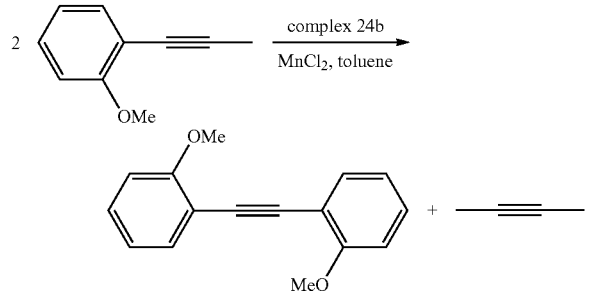

In a dry 25 mL Schlenk-tube, which has been flooded with argon, complex 24b (58 mg, 0.05 mmol, 5 mol %) and MnCl₂ (6.3 mg, 0.05 mmol) were dissolved in 1 mL of toluene. Subsequently, the mixture was heated for 30 to 80° C. and was re-cooled to room temperature. The solution of the catalyst was transferred into a suspension of 1-methoxy-2-(prop-1-inyl)benzene (325 mg, 1 mmol) and molecular sieve (1 g, 5 Å, powder) in 4 mL of toluene and the reaction mixture was stirred for 2 h at room temperature. Subsequently, it was filtered over a short silica gel column (2 cm), the filtrate was concentrated and the residue was purified by means of column chromatography (SiO₂, hexane/EtOAc, 20:1). One obtains 1,2-bis(2-methoxyphenyl)ethine (116 mg, 97%) as colorless solid. M.p.=126-127° C.; ¹H NMR (400 MHz, CD₂Cl₂): δ=7.49 (ddd, J=7.3, 1.6, 0.5 Hz, 2H), 7.33 (ddd, J=7.9, 7.7, 1.9 Hz, 2H), 6.95 (td, J=7.9, 1.0 Hz, 4H), 3.92 (s, 6H); ¹³C NMR (100 MHz, CD₂Cl₂): δ=160.3 (2×C), 133.7 (2×CH), 130.1 (2×CH), 120.8 (2×CH), 113.0 (2×C), 111.3 (2×CH), 90.1 (2×C), 56.2 (2×CH₃); IR (film): ν=3105, 3033, 2998, 2963, 2937, 2833, 1945, 1903, 1863, 1598, 1574, 1498, 1464, 1456, 1432, 1274, 1241, 1184, 1162, 1115, 1047, 1020, 937, 750 cm⁻¹; MS (EI) m/z (%): 238 [M⁺] (100), 237 (32), 223 (23), 221 (15), 207 (10), 195 (5), 178 (8), 165 (14), 152 (9), 131 (19), 111 (6), 97 (3), 89 (3); HRMS (ESI): m/z: calculated for C₁₆H₁₄O₂+Na: 261.0886. found: 261.0884.

For further examples of compounds, which were synthesized in an analogous manner, see Tables 1 and 2.

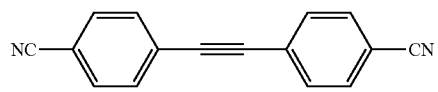

Orange solid. M.p.=252-255° C.; ¹H NMR (CDCl₃, 400 MHz): δ=8.27 (d, J=8.8 Hz, 4H), 7.73 (d, J=8.8 Hz, 4H); ¹³C NMR (CDCl₃, 100 MHz): δ=147.3, 134.6, 132.3, 128.5, 127.6, 123.4, 91.6; IR (film, cm⁻¹): 3058, 2920, 2225, 1928, 1675, 1606, 1502, 1408, 1273, 1182, 1022, 841, 553; MS (EI) m/z (%): 228 [M⁺] (100), 201 (8), 175 (4), 151 (3), 137 (1), 100 (3), 87 (4), 74 (3), 63 (1). The analytical and spectroscopic data correspond to those of the literature (Pschirer, N. G.; Bunz, U. H. F. *Tetrahedron Lett.* 1999, 40, 2481).

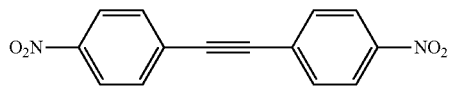

Yellow solid. M. P.=205-207° C.; ¹H NMR (CDCl₃, 400 MHz): δ=7.68 (d, J=8.5 Hz, 4H), 7.64 (d, J=8.5 Hz, 4H); ¹³C NMR (CDCl₃, 100 MHz): δ=132.4, 132.3, 127.2, 118.4, 112.6, 91.7; IR (film, cm⁻¹): 3058, 2920, 2254, 2225, 1928, 1675, 1606, 1502, 1408, 1273, 1182, 1022, 841, 553; MS (EI) m/z (%): 268 [M⁺] (100), 238 (23), 222 (7), 210 (4), 192 (6), 176 (42), 163 (19), 150 (15), 137 (4), 126 (5), 111 (2), 99 (4), 75 (7), 63 (4), 51 (3); HRMS (ESI): m/z: calculated for C₁₄H₈N₂O₄: 268.0484; found: 268.0485. The analytical and spectroscopic data correspond to those of the literature (Akiyama, S; Tajima, K; Nakatsuji, S.; Nakashima, K.; Abiru, K.; Watanabe, M. *Bull. Chem. Soc. Jpn.* 1995, 68, 2043).

14. Alkyne Cross-Metathesis Using [Mo(≡CPh)(OSiPh₃)₃(bipy)] (24b) and MnCl₂

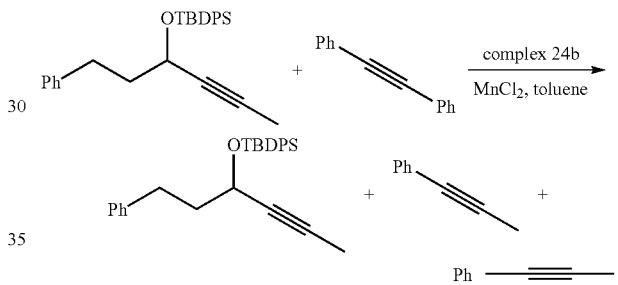

In a dry 25 mL Schlenk-tube, which has been flooded with argon, complex 24b (58 mg, 0.05 mmol, 5 mol %) and MnCl₂ (6.3 mg, 0.05 mmol) were suspended in toluene (1 mL) and were subsequently heated for 30 min to 80° C. After cooling to room temperature, the formed suspension was added to a suspension of tert-butyldiphenyl-(1-phenylhex-4-ine-3-oxy)silane (412 mg, 1.00 mmol), tolane (446 Mg, 2.50 mmol) and molecular sieve (1 g, 5 Å, powder) in toluene (4 mL), and the formed mixture was stirred for 24 h at room temperature. For processing, it is filtered through a short silica gel column, the filtrate is concentrated and the residue is purified by means of column chromatography (hexane). One obtains tert-butyl-(1,5-diphenylpent-1-ine-3-oxy)-diphenylsilane as colorless solid (336 mg, 71%). ¹H NMR (400 MHz, CDCl₃): δ(ppm)=7.82-7.80 (m, 2H), 7.75-7.72 (m, 2H), 7.50-7.34 (m, 6H), 7.29-7.15 (m, 10H), 4.63 (t, J=6.1 Hz, 1H), 2.87-2.82 (m, 2H), 2.13-2.07 (m, 2H), 1.13 (s, 9H); ¹³C NMR (100 MHz, CDCl₃): δ(ppm)=141.8, 136.1, 135.9, 133.8, 133.7, 131.5, 129.7, 129.5, 128.4, 128.3, 128.1, 128.0, 127.6, 127.4, 125.8, 123.0, 90.4, 85.3, 63.8, 40.1, 31.3, 27.0, 19.4; IR (film): ν=3070, 3026, 2931, 2892, 2857, 1599, 1589, 1489, 1472, 1454, 1443, 1390, 1361, 1341, 1258, 1170, 1156, 1105, 1084, 1050, 1029, 1007, 998, 979, 938, 908, 843, 821, 798, 755, 734, 698, 689 cm⁻¹; MS (EI) m/z (%): 474 [M⁺] (3), 417 (23), 369 (2), 339 (100), 313 (4), 283 (62), 223 (4) 199 (20), 181 (5), 135 (3), 91 (12), 77 (3); HRMS (ESI): m/z: calculated for C₃₃H₃₄OSi: 474.2379; found: 474.2379.

The invention claimed is:
1. Metal-organic compounds of the general Formula I,

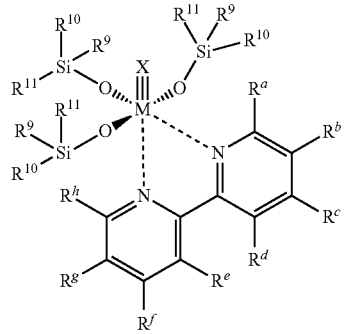

(I)

wherein
M is selected from Mo or W,
the substituents $R^a$, $R^b$, $R^c$, $R^d$, $R^e$, $R^f$, $R^g$, $R^h$ may be equal or may be different from one another and are selected independently from one another from: H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, nitro, cyano, trifluoromethyl, or —$COOR^{12}$, wherein $R^{12}$ is selected from $C_1$-$C_{12}$-alkyl, $C_3$-$C_{12}$-cycloalkyl, 6-18 membered aryl, or 5-10 membered heteroaryl,
and the substituents $R^a$ and $R^b$ or $R^b$ and $R^c$ or $R^c$ and $R^d$ and $R^h$ and $R^g$ or $R^g$ and $R^f$ or $R^f$ and $R^e$ may optionally also be linked together while forming a saturated, unsaturated or aromatic ring,
and/or the residues $R^d$ and $R^e$ may optionally be linked together while forming a 5-8 membered saturated, unsaturated or aromatic ring,
the substituents $R^9$, $R^{10}R^{11}$ may be equal or may be different from one another and are independently selected from one another from the following groups: $C_1$-$C_{12}$-alkyl, $C_3$-$C_{12}$-cycloalkyl, 6-18 membered aryl, or 5-10 membered heteroaryl, with the proviso that at least one of said substituents is a 6-18 membered aryl or 5-10 membered heteroaryl residue, wherein said aryl or heteroaryl residue at the silicon in turn has up to five identical or different substituents, from the list: H, $C_1$-$C_{12}$-alkyl, $C_1$-$C_{12}$-alkyloxy, di-$C_1$-$C_4$-alkylamino, $C_3$-$C_{12}$-cycloalkyl, $C_3$-$C_{12}$-cycloalkyloxy, 6-18 membered aryl, 5-10 membered heteroaryl, or halogen, and X is selected from N or $CR^{13}$, wherein $R^{13}$ is selected from $C_1$-$C_{12}$-alkyl, $C_3$-$C_{12}$-cycloalkyl, 6-18 membered aryl, or 5-10 membered heteroaryl.

2. Metal-organic compound according to claim 1, characterized in that the residues $R^d$ and $R^e$ are linked together while forming a 5-8 membered saturated, unsaturated or aromatic ring, and thus form a bridge, which selected from $CR^{41}R^{42}$, $CR^{43}$=$CR^{44}$, $CR^{45}R^{46}$—$CR^{47}R^{48}$, $CR^{49}R^{50}$—$CR^{51}R^{52}$—$CR^{53}R^{54}$, $CR^{55}R^{56}$=$C^{57}R^{58}$—$CR^{59}R^{60}$, $CR^{61}R^{62}$—$CR^{63}R^{65}$—$CR^{65}R^{66}$—$CR^{67}CR^{68}$, $CR^{69}$=$CR^{70}$—$CR^{71}R^{72}$—$CR^{73}CR^{74}$ or $CR^{75}R^{76}$—$CR^{77}$=$CR^{78}$—$CR^{79}CR^{80}$ in which $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$ and $R^{80}$ are independently selected from one other and may have the same meaning as $R^a$ as defined in claim 1.

3. Metal-organic compounds according to claim 2, characterized in that the phenanthroline ligand in Formula 11 is selected from: 1,10-phenanthroline, 4-methyl-1,20-phenanthroline, 5-methyl-1,10-phenanthroline, 2,9-dimethyl[1,10]-phenanthroline, 5,6-dimethyl-1,10-phenanthroline, 5-chloro[1,10]phenanthroline, 4,7-dichloro-1,10-phenanthroline, 4,7-dichloro-1,10-phenanthroline, 3,4,7,8-tetramethyl-1,10-phenanthroline, 4,7-diphenyl[1,10]phenanthroline, 2,9-dimethyl-4,7-diphenyl[1,10]phenanthroline, 5-nitro-1,10-phenanthroline, or 4,7-dimethoxy-1,10-phenanthroline.

4. Metal-organic compounds according to claim 1, which are represented by the general Formula 11

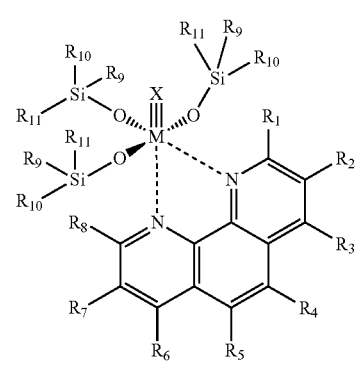

11 wherein
the substituents $R^1$, $R^2$, $R^3$, $R^4$, $R^5$, $R^6$, $R^7$, $R^8$ may be equal or may be different from one another and are independently selected from one another from H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, or nitro, and M, X, $R^9$, $R^{10}$ and $R^{11}$ are defined as defined in claim 1.

5. Metal-organic compounds according to claim 1, which are represented by the general Formula 11a

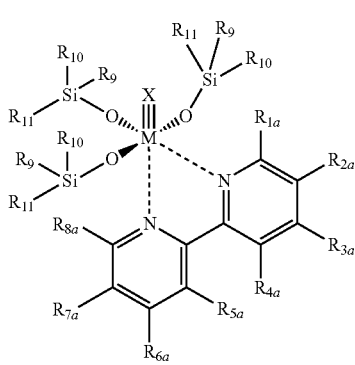

11a wherein
$R^{1a}$, $R^{2a}$, $R^{3a}$, $R^{4a}$, $R^{5a}$, $R^{6a}$, $R^{7a}$, $R^{8a}$ may be equal or may be different from one another and are independently selected from one another from: H, $C_1$-$C_{12}$-alkyl, $C_3$-$C_{12}$-cycloalkyl, 6-18 membered aryl, 5-10 membered heteroarlyl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, or nitro, and M, X, $R^9$, $R^{10}$ and $R^{11}$ are defined as defined in claim 1.

6. Metal-organic compounds according to claim 1, characterized in that the bipyridyl ligand is selected from: 2,2'-bipyridine, 5,5'-dimethyl-2,2'-dipyridyl, 4,4'-dimethyl-2,2'-dipyridyl, 6,6'-dimethyl-2,2'-dipyridyl, 4,4'-dimethoxy-2,2'-bipyridine, 2,2'-biquinoline, 4,4'-di-tert-butyl-2,2'-dipyridyl, 2,2'-bipyridinyl-4,4'-dicarboxylic acid dimethyl ester, 4,4'-diphenyl-2,2'-dipyridyl, 6,6'-dibromo-2,2'-dipyridyl, 4,4'-dinonyl-2,2'-dipyridyl, 2,2'-biquinolinyl-4,4'-dicarboxylic acid dibutyl ester, 2,2'-biquinolinyl-4,4'-dicarboxylic acid diheptyl ester, 6-methyl-2,2'-dipyridyl, 2-(2-pyridinyl)quinoline, 2-pyridin-2-yl-4-pyrrolidin-1-yl-quinoline, 4-piperidin-1-yl-2-pyridin-2-yl-quinoline, or 4-morpholin-4-yl-2-pyridin-2-yl-quinoline.

7. Metal-organic compounds according to one of claim 1, characterized in that $R^9$, $R^{10}$, and $R^{11}$ are phenyl, respectively.

8. Metal-organic compounds according to claim 1, which are represented by the general Formula 12

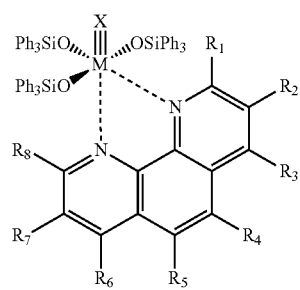

12 wherein

M is selected from Mo or W,

X is selected from N or $CR^{13}$, wherein $R^{13}$ may be methyl, ethyl, propyl, butyl, iso-propyl, tert-butyl, trimethylsilylmethyl, benzyl, furyl, or phenyl, wherein phenyl in turn may bear up to five identical or different residues from the list: H, methyl, ethyl, propyl, butyl, tert-butyl, iso-propyl, phenyl, fluorine, chlorine, trifluoromethyl, methoxy, ethoxy, dimethylamino, diethylamino, or trimethylsilyl, $R^1$, $R^2$, $R^3$, $R^4$, $R^5$, $R^6$, $R^7$, $R^8$ are freely and independently selected from one another from: H, $C_1$-$C_4$ alkyl, $C_3$-$C_6$ cycloalkyl, phenyl, naphthyl, methylphenyl, dimethylphenyl, trimethylphenyl, methoxyphenyl, dimethoxyphenyl, fluorophenyl, pentafluorophenyl, trifluoromethylphenyl, dimethylaminophenyl, furyl, halogen, nitro, cyano, trifluoromethyl, or —$COOR^{12}$, wherein $R^{12}$ is selected from $C_1$-$C_{12}$ alkyl, $C_3$-$C_{12}$ cycloalkyl, 6-18 membered aryl, or 5-10 membered heteroaryl.

9. Metal-organic compounds according to claim 1, which are represented by the general Formula 12a

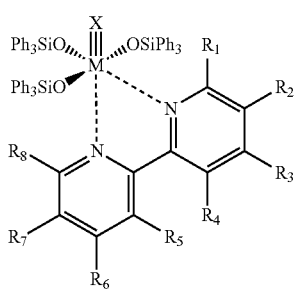

12a wherein

M is selected from Mo or W,

X is selected from N or $CR^{13}$, wherein $R^{13}$ is methyl, ethyl, propyl, butyl, iso-propyl, tert-butyl, trimethylsilylmethyl, benzyl, furyl, or phenyl, wherein phenyl in turn may bear up to five identical or different residues from the list: H, methyl, ethyl, propyl, butyl, tert-butyl, iso-propyl, phenyl, fluorine, chlorine, trifluoromethyl, methoxy, ethoxy, dimethylamino, diethylamino, or trimethylsilyl, $R_1$, $R_2$, $R_3$, $R_4$, $R_5$, $R_6$, $R_7$, $R_8$ are freely and independently selected from one another from: H, $C_1$-$C_4$ alkyl, $C_3$-$C_6$ cycloalkyl, phenyl, naphthyl, methylphenyl, dimethylphenyl, trimethylphenyl, methoxyphenyl, dimethoxyphenyl, fluorophenyl, pentafluorophenyl, trifluoromethylphenyl, furyl, halogen, nitro, or —$COOR^{12}$ wherein $R^{12}$ is selected from $C_1$-$C_{12}$ alkyl, $C_3$-$C_{12}$ cycloalkyl, 6-18 membered aryl, or 5-10 membered heteroaryl.

10. Metal-organic compounds according to claim 1, which are represented by the Formulas 13a, 13b, 13c, 13d, 13e

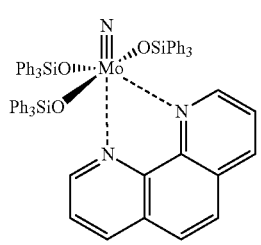

13a

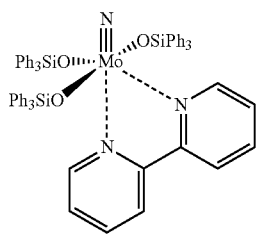

13b

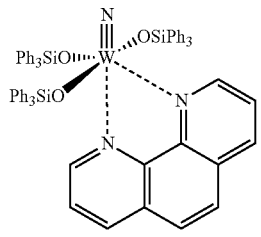

13c

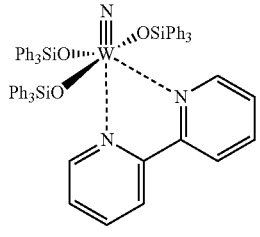

13d

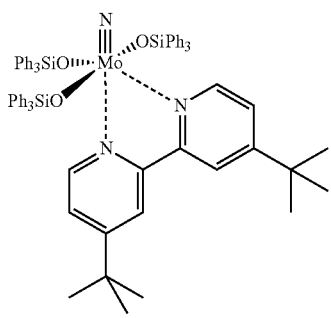
13e

11. Metal-organic compounds according to claim 1, which are represented by the Formulas 14a, 14b, 15a, 15b, 16a, 16b

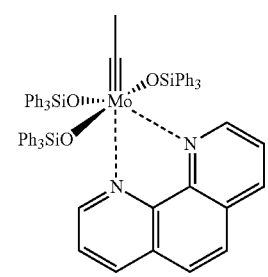
14a

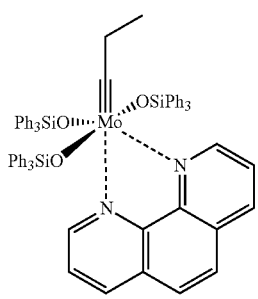
15a

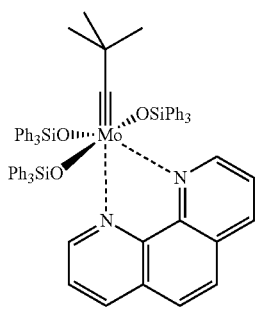
16a

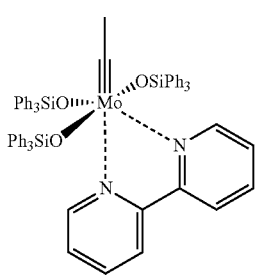
14b

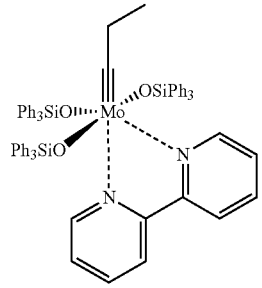
15b

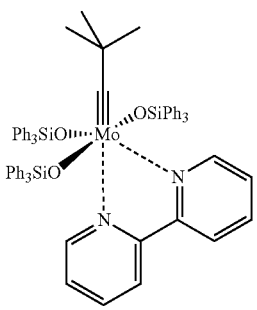
16b

12. Metal-organic compounds according to claim 1, which are represented by the Formulas 17a or 17b

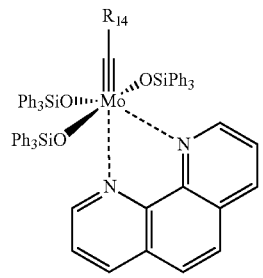
17a

17b wherein $R^{14}$ is a phenyl ring, which bears from 1 to 5 equal or different substituents, selected from the list: H, methyl, ethyl, propyl, butyl, tert-butyl, iso-propyl, phenyl, fluorine, chlorine, trifluoromethyl, methoxy, ethoxy, dimethylamino, diethylamino, or trimethylsilyl.

13. Metal-organic compounds according to claim 12, which are represented by the Formulas 24a, 24b, 24c, 24d, 24e, 34a

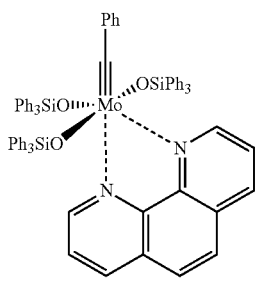
24a

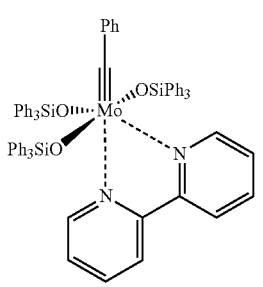
24b

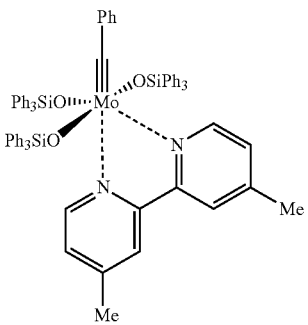
24c

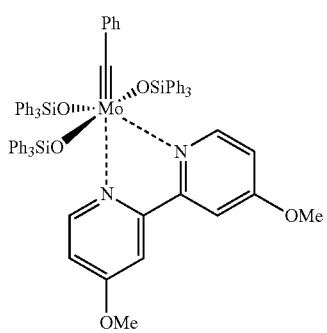
24d

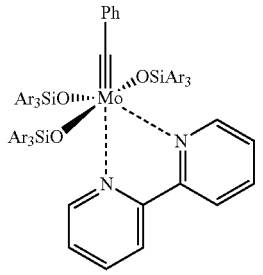
24e

Ar = 4-Methoxyphenyl

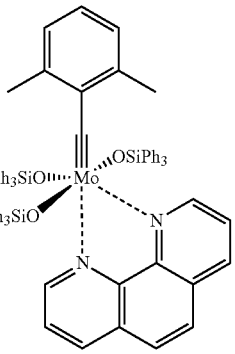
34a

14. Use of the compounds according to claim 1 as pre-catalysts for carrying out alkyne metathesis reactions.

15. Alkylidyne complexes of the general Formula 25

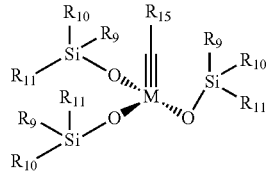
25 wherein

M is selected from Mo or W, the substituents $R^9$, $R^{10}$, $R^{11}$ may be equal or may be different from one another and are independently selected from one another from the following groups: $C_1$-$C_{12}$-alkyl, $C_3$-$C_{12}$-cycloalkyl, 6-18 membered aryl, or 5-10 membered heteroaryl, with the proviso that at least one of said substituents is a 6-18 membered aryl or 5-10 membered heteroaryl residue, wherein said aryl or heteroaryl residue at the silicon in turn has up to five identical or different substituents, from the list: H, $C_1$-$C_{12}$-alkyl, $C_1$-$C_{12}$-alkyloxy, di-$C_1$-$C_4$-alkylamino, $C_3$-$C_{12}$-cycloalkyl, $C_3$-$C_{12}$-cycloalkyloxy, 6-18 membered aryl, 5-10 membered heteroaryl, or halogen, and, $R^{15}$ is selected from $C_1$-$C_{12}$ alkyl, $C_3$-$C_{12}$ cycloalkyl, 6-18 membered aryl, or 5-10 membered heteroaryl.

16. Adducts of alkylidyne complexes of the general Formula 25 according to claim 15 with solvents, which may be selected from the list: acetonitrile, benzonitrile, pivalonitrile, diethyl ether, diisopropyl ether, tert-butylmethyl ether, diphenyl ether, methoxybenzene, tetrahydrofuran, dioxane, or dimethoxyethane, and the use as catalysts for such alkyne metathesis reactions.

17. Alkylidyne complexes according to claim 15, characterized in that $R^9$, $R^{10}$ and $R^{11}$ are phenyl, respectively.

18. Alkylidyne complexes according to claim 15, characterized in that $R^{15}$ is methyl, ethyl, propyl, butyl, iso-propyl, tert-butyl, trimethylsilylmethyl, benzyl, (dimethyl)(phenyl)methyl, phenyl, methylphenyl, dimethylphenyl, trimethylphenyl, methoxyphenyl, dimethoxyphenyl, fluorophenyl, pentafluororophenyl, trifluoromethylphenyl, or furyl.

19. Use of the compounds of Formula 25 and the adducts with solvents thereof

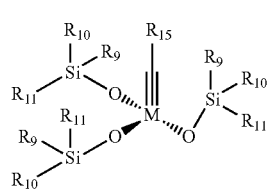

wherein

M is selected from Mo or W, the substituents $R^9$, $R^{10}$, $R^{11}$ may be equal or may be different from one another and are independently selected from one another from the following groups: $C_1$-$C_{12}$-alkyl, $C_3$-$C_{12}$-cycloalkyl, 6-18 membered aryl, or 5-10 membered heteroaryl, with the proviso that at least one of said substituents is a 6-18 membered aryl or 5-10 membered heteroaryl residue, wherein said aryl or heteroaryl residue at the silicon in turn has up to five identical or different substituents, from the list: H, $C_1$-$C_{12}$-alkyl, $C_1$-$C_{12}$-alkyloxy, di-$C_1$-$C_4$-alkylamino, $C_3$-$C_{12}$-cycloalkyl, $C_3$-$C_{12}$-cycloalkyloxy, 6-18 membered aryl, 5-10 membered heteroaryl, or halogen, and $R^{15}$ is selected from $C_1$-$C_{12}$ alkyl, $C_3$-$C_{12}$ cycloalkyl, 6-18 membered aryl, or 5-10 membered heteroaryl, as catalysts for the alkyne metathesis.

20. Method according to claim 19, characterized in that the compound of Formula 19 is selected from derivatives of 1,10-phenanthroline or 2,2'-bipyridine.

21. Method of preparing the compounds of Formula I

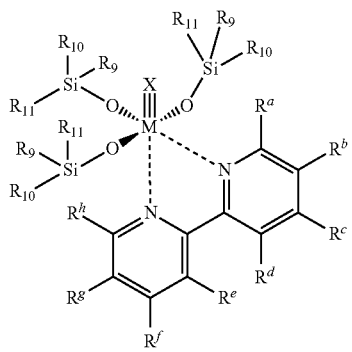

(I)

wherein

M is selected from Mo or W, the substituents $R^a$, $R^b$, $R^c$, $R^d$, $R^e$, $R^f$, $R^g$, $R^h$ may be equal or may be different from one another and are selected independently from one another from: H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, nitro, cyano, trifluoromethyl, or —$COOR^{12}$, wherein $R^{12}$ is selected from $C_1$-$C_{12}$-alkyl, $C_3$-$C_{12}$-cycloalkyl, 6-18 membered aryl, or 5-10 membered heteroaryl, and the substituents $R^a$ and $R^b$ or $R^b$ and $R^c$ or $R^c$ and $R^d$ and $R^h$ and $R^g$ or $R^g$ and $R^f$ or $R^f$ and $R^e$ may optionally also be linked together while forming a saturated, unsaturated or aromatic ring, and/or the residues $R^d$ and $R^e$ may optionally be linked together while forming a 5-8 membered saturated, unsaturated or aromatic ring, the substituents $R^9$, $R^{10}$, $R^{11}$ may be equal or may be different from one another and are independently selected from one another from the following groups: $C_1$-$C_{12}$-alkyl, $C_3$-$C_{12}$-cycloalkyl, 6-18 membered aryl, or 5-10 membered heteroaryl, with the proviso that at least one of said substituents is a 6-18 membered aryl or 5-10 membered heteroaryl residue, wherein said aryl or heteroaryl residue at the silicon in turn has up to five identical or different substituents, from the list: H, $C_1$-$C_{12}$-alkyl, $C_1$-$C_{12}$-alkyloxy, di-$C_1$-$C_4$-alkylamino, $C_3$-$C_{12}$-cycloalkyl, $C_3$-$C_{12}$-cycloalkyloxy, 6-18 membered aryl, 5-10 membered heteroaryl, or halogen, and X is selected from N or $CR^{13}$, wherein $R^{13}$ is selected from $C_1$-$C_{12}$-alkyl, $C_3$-$C_{12}$-cycloalkyl, 6-18 membered aryl, or 5-10 membered heteroaryl in which a compound of the general Formula 18

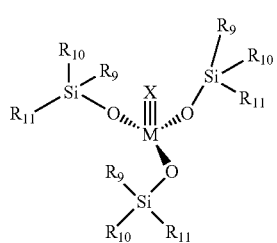

18 is reacted with a compound of the general Formula 19

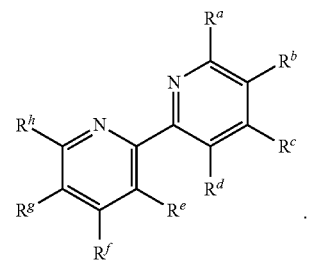

19

22. Method for carrying out alkyne metathesis reactions, in which a compound of the general Formula I

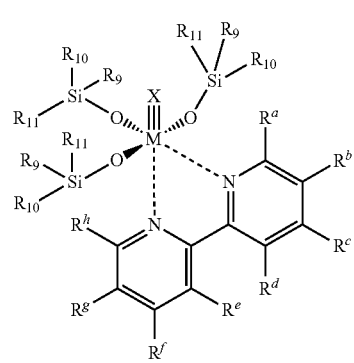

(I)

wherein

M is selected from Mo or W, the substituents $R^a$, $R^b$, $R^c$, $R^d$, $R^e$, $R^f$, $R^g$, $R^h$ may be equal or may be different from one another and are selected independently from one another from: H, $C_1$-$C_{12}$-alkyl, $C_3$-$C_{12}$-cycloalkyl, 6-18 membered aryl, 5-10 membered heteroaryl, $C_1$-$C_{12}$-alkyloxy, $C_3$-$C_{12}$-cycloalkyloxy, $C_6$-$C_{20}$-aryloxy, di-$C_1$-$C_4$-alkylamino, halogen, nitro, cyano, trifluoromethyl, or —COOR$^{12}$, wherein R$^{12}$ is selected from $C_1$-$C_{12}$-alkyl, $C_3$-$C_{12}$-cycloalkyl, 6-18 membered aryl, or 5-10 membered heteroaryl, and the substituents R$^a$ and R$^b$ or R$^b$ and R$^c$ or R$^c$ and R$^d$ and R$^h$ and R$^g$ or R$^g$ and R$^f$ or R$^f$ and R$^e$ may optionally also be linked together while forming a saturated, unsaturated or aromatic ring, and/or the residues R$^d$ and R$^e$ may optionally be linked together while forming a 5-8 membered saturated, unsaturated or aromatic ring, the substituents R$^9$, R$^{10}$, R$^{11}$ may be equal or may be different from one another and are independently selected from one another from the following groups: $C_1$-$C_{12}$-alkyl, $C_3$-$C_{12}$-cycloalkyl, 6-18 membered aryl, or 5-10 membered heteroaryl, with the proviso that at least one of said substituents is a 6-18 membered aryl or 5-10 membered heteroaryl residue, wherein said aryl or heteroaryl residue at the silicon in turn has up to five identical or different substituents, from the list: H, $C_1$-$C_{12}$-alkyl, $C_1$-$C_{12}$-alkyloxy, di-$C_1$-$C_4$-alkylamino, $C_3$-$C_{12}$-cycloalkyl, $C_3$-$C_{12}$-cycloalkyloxy, 6-18 membered aryl, 5-10 membered heteroaryl, or halogen, and X is selected from N or CR$^{13}$, wherein R$^{13}$ is selected from $C_1$-$C_{12}$-alkyl, $C_3$-$C_{12}$-cycloalkyl, 6-18 membered aryl, or 5-10 membered heteroaryl, is reacted in presence of a metal salt.

23. Method according to claim 22, characterized in that the metal salt is selected from: MnY$_2$, FeY$_2$, FeY$_3$, CoY$_2$, CuY$_2$, ZnY$_2$, MgY$_2$, NiY$_2$, PdY$_2$, PtY$_2$, RuY$_2$, RuY$_3$, or EuY$_3$, wherein Y is selected from F, Cl, Br, I, acetylacetonate, sulfate, sulfonate, nitrate, acetate, or trifluoroacetate.

24. Method according to claim 22, characterized in that the alkyne metathesis reaction is carried out in presence of a molecular sieve.

25. Method according to claim 22, characterized in that the alkyne metathesis reaction is carried out in presence of molecular sieve 4 Ångström (MS 4 Å) or molecular sieve 5 Ångström (MS 5 Å).

* * * * *

UNITED STATES PATENT AND TRADEMARK OFFICE
CERTIFICATE OF CORRECTION

PATENT NO.        : 8,993,470 B2
APPLICATION NO.   : 13/639067
DATED             : March 31, 2015
INVENTOR(S)       : Alois Fuerstner et al.

Page 1 of 1

It is certified that error appears in the above-identified patent and that said Letters Patent is hereby corrected as shown below:

In the specification

Column 5, Line 14 reads, "... $CR^{49}R^{50}-R^{51}R^{52}-$ ..." which should read "... $CR^{49}R^{50}-CR^{51}R^{52}-$ ..."

Column 20, Line 62 reads, "(2 mg per pmol of released 2-butine)" which should read "(2 mg per μmol of released 2-butine)"

Column 29, Line 1 reads, "... 697 $cm^{1}$;" which should read "... 697 $cm^{-1}$;"

Column 38, Line 30 reads, "... calculated for $O_{16}H_{14}O_2$ + Na:" which should read "... calculated for $C_{16}H_{14}O_2$ + Na:"

Column 39, Line 42 reads, "... calculated for $O_{18}H_{14}O_4$ + Na: 317.0784; ..." which should read "... calculated for $C_{18}H_{14}O_4$ + Na: 317.0784; ..."

Column 40, Line 32 reads, "... calculated for $O_{10}H_6S_2$ : ..." which should read "... calculated for $C_{10}H_6S_2$ : ..."

In the claims

Column 58, Line 44 reads, "... $C_1$-$C_{12}$-alkvloxy, ..." which should read "... $C_1$-$C_{12}$-alkyloxy, ..."

Column 59, Line 22 reads, "... $C_1$-$C_{12}$-alkvloxy, ..." which should read "... $C_1$-$C_{12}$-alkyloxy, ..."

Signed and Sealed this
Twenty-second Day of December, 2015

Michelle K. Lee
*Director of the United States Patent and Trademark Office*